(12) United States Patent
Song et al.

(10) Patent No.: US 12,312,402 B2
(45) Date of Patent: May 27, 2025

(54) ANTIBODY OR CHIMERIC ANTIGEN RECEPTOR WHICH TARGETS CLAUDIN 18.2

(71) Applicant: SHANDONG BOAN BIOTECHNOLOGY CO., LTD., Shandong (CN)

(72) Inventors: Deyong Song, Shandong (CN); Li Zhou, Woburn, MA (US); Chuangchuang Dong, Shandong (CN); Zhenfei Ning, Shandong (CN)

(73) Assignee: Shandong Boan Biotechnology Co., Ltd., Yantai (CN)

( * ) Notice: Subject to any disclaimer, the term of this patent is extended or adjusted under 35 U.S.C. 154(b) by 877 days.

(21) Appl. No.: 17/601,765

(22) PCT Filed: May 28, 2020

(86) PCT No.: PCT/CN2020/092849
§ 371 (c)(1),
(2) Date: Oct. 6, 2021

(87) PCT Pub. No.: WO2020/239005
PCT Pub. Date: Dec. 3, 2020

(65) Prior Publication Data
US 2022/0204609 A1 Jun. 30, 2022

(30) Foreign Application Priority Data

May 30, 2019 (CN) .......................... 201910459129.1
May 30, 2019 (CN) .......................... 201910459622.3

(51) Int. Cl.
| | |
|---|---|
| *C07K 16/28* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 5/10* | (2006.01) |
| *C12N 15/00* | (2006.01) |
| *C12N 15/63* | (2006.01) |
| *G01N 33/563* | (2006.01) |
| *G01N 33/574* | (2006.01) |
| *A61K 39/00* | (2006.01) |
| *C12N 5/16* | (2006.01) |
| *G01N 33/53* | (2006.01) |

(52) U.S. Cl.
CPC .............. *C07K 16/28* (2013.01); *A61K 40/11* (2025.01); *A61K 40/31* (2025.01); *A61K 40/4202* (2025.01); *A61P 35/00* (2018.01); *C07K 14/7051* (2013.01); *C07K 14/70517* (2013.01); *C07K 14/70578* (2013.01); *A61K 2039/505* (2013.01); *A61K 2239/38* (2023.05); *A61K 2239/51* (2023.05); *C07K 2317/73* (2013.01); *C07K 2317/732* (2013.01); *C07K 2317/76* (2013.01); *C07K 2317/92* (2013.01); *C07K 2319/03* (2013.01); *C07K 2319/33* (2013.01); *C12N 5/10* (2013.01); *C12N 5/16* (2013.01); *C12N 15/63* (2013.01); *C12N 2800/00* (2013.01); *G01N 33/53* (2013.01)

(58) Field of Classification Search
CPC ................ C07K 16/28; C07K 2317/52; C07K 2317/622; C07K 2317/72; C07K 2317/73; C07K 2317/732; C07K 2317/76; C07K 2317/92; C07K 2319/03; C07K 2319/33; A61K 40/11; A61K 40/31; A61K 40/4202; A61K 2039/505; A61P 35/00; A01K 2227/105
See application file for complete search history.

(56) References Cited

U.S. PATENT DOCUMENTS

| | | |
|---|---|---|
| 2011/0059095 A1 | 3/2011 | MacDonald et al. |
| 2015/0374789 A1 | 12/2015 | Sahin et al. |
| 2018/0282389 A1 | 10/2018 | Sahin et al. |

(Continued)

FOREIGN PATENT DOCUMENTS

| | | |
|---|---|---|
| CN | 102139106 | 8/2011 |
| CN | 102574923 | 7/2012 |
| CN | 104427999 | 3/2015 |

(Continued)

OTHER PUBLICATIONS

Almasbak, Hilde, Aarvak, Tanja, Vemuri, Mohan C., CAR T Cell Therapy: A Game Changer in Cancer Treatment, Journal of Immunology Research, 2016, 5474602, 10 pages, 2016. https://doi.org/10.1155/2016/5474602 (Year: 2016).*

(Continued)

*Primary Examiner* — Hong Sang
(74) *Attorney, Agent, or Firm* — Fish & Richardson P.C.

(57) ABSTRACT

Disclosed are an antibody or an antigen binding fragment or chimeric antigen receptor thereof which binds to Claudin18.2, and a preparation method and a use. The chimeric antigen receptor sequentially comprises the antibody or the antigen binding fragment thereof which binds to the Claudin18.2 antigen, an extracellular hinge region, a transmembrane region and an intracellular signaling region. The antibody or the antigen binding fragment or chimeric antigen receptor thereof has stronger affinity and killing capability for cells secreting Claudin18.2, and a better tumor inhibiting effects.

20 Claims, 11 Drawing Sheets
Specification includes a Sequence Listing.

(56) References Cited

U.S. PATENT DOCUMENTS

2019/0117691 A1* 4/2019 Li .................. C12N 15/62

FOREIGN PATENT DOCUMENTS

| CN | 103571872 | 11/2016 | | |
|---|---|---|---|---|
| CN | 109206524 | 1/2019 | | |
| CN | 109762067 | 5/2019 | | |
| EP | 1749029 | 2/2007 | | |
| JP | 2015-517476 | 6/2015 | | |
| JP | 2015-518838 | 7/2015 | | |
| JP | 2016-510721 | 4/2016 | | |
| JP | 2016-517447 | 6/2016 | | |
| WO | WO 2005118644 | 12/2005 | | |
| WO | WO 2011031695 | 3/2011 | | |
| WO | WO 2013167259 | 11/2013 | | |
| WO | WO 2013174404 | 11/2013 | | |
| WO | WO 2014075697 | 5/2014 | | |
| WO | WO 2014075788 | 5/2014 | | |
| WO | WO 2014127785 | 8/2014 | | |
| WO | WO 2014146672 | 9/2014 | | |
| WO | WO 2016008405 | 1/2016 | | |
| WO | WO 2016165762 | 10/2016 | | |
| WO | WO 2017041749 | 3/2017 | | |
| WO | WO 2017189964 | 11/2017 | | |
| WO | WO 2018006882 | 1/2018 | | |
| WO | WO 2018091661 | 5/2018 | | |
| WO | WO-2013004841 A1 * | 4/2019 | .............. | A61P 35/00 |

OTHER PUBLICATIONS

Chailyan A, Marcatili P, Tramontano A. The association of heavy and light chain variable domains in antibodies: implications for antigen specificity. FEBS J. Aug. 2011;278(16):2858-66. doi: 10.1111/j.1742-4658.2011.08207.x. Epub Jun. 28, 2011. PMID: 21651726; PMCID: PMC3562479. (Year: 2011).*

Chiu. "Antibody Structure and Function: The Basis for Engineering Therapeutics". Antibodies 2019, 8(4), 55; https://doi.org/10.3390/antib8040055 (Year: 2019).*

Boonyaratanakornkita. "Monoclonal antibodies for prophylaxis and treatment of respiratory viral infections". Curr Opin Infect Dis. 2022; 35(4):280-287 (Year: 2022).*

ClinicalTrials.gov [online], "Efficacy and Safety of IMAB362 in Combination With the EOX Regimen for CLDN18.2-positive Gastric Cancer (FAST)," NCT01630083, last updated Jan. 18, 2020, retrieved on Apr. 21, 2022, retrieved from URL <https://clinicaltrials.gov/ct2/show/study/NCT01630083> 22 pages.

Extended European Search Report in European Appln. No. 20815562.2, dated May 23, 2022, 14 pages.

International Preliminary Report on Patentability in International Appln. No. PCT/CN2020/092849, dated Nov. 16, 2021, 29 pages.

International Search Report and Written Opinion in International Appln. No. PCT/CN2020/092849, dated Oct. 13, 2020, 13 pages.

Jiang et al., "Claudin18.2-Specific Chimeric Antigen Receptor Engineered T Cells for the Treatment of Gastric Cancer", J. Natl. Cancer Inst., Jan. 2019, 111(4):409-418.

Niimi et al., "Claudin-18, a novel downstream target gene for the T/EBP/NKX2. 1 homeodomain transcription factor, encodes lung- and stomach-specific isoforms through alternative splicing," Mol Cell Biol, Nov. 2001, 21(21):7380-90.

Sahin et al., "Claudin-18 splice variant 2 is a pan-cancer target suitable for therapeutic antibody development," Clin. Cancer Res., Dec. 2008, 14(23):7624-7634.

Singh et al., "Anti-claudin 18.2 antibody as new targeted therapy for advanced gastric cancer," J. Hematol. Oncol., 2017, 10:105, 5 pages.

Woll et al., "Claudin 18.2 is a target for IMAB362 antibody in pancreatic neoplasms", Int. J. Cancer, Sep. 2013, 134(3):731-9.

Zuo et al., "Potential role of Claudin-18 in treatment of gastric cancer," Chin J of Clinicians (Electronic Edition), Feb. 2018, 12(3):173-176 (with English Abstract).

* cited by examiner

SEQUENCE LISTING

```
<160> NUMBER OF SEQ ID NOS: 46

<210> SEQ ID NO 1
<211> LENGTH: 107
<212> TYPE: PRT
<213> ORGANISM: Homo sapiens

<400> SEQUENCE: 1

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95
```

```
Thr Phe Gly Gln Gly Thr Lys Val Glu Ile Lys
            100                 105

<210> SEQ ID NO 2
<211> LENGTH: 124
<212> TYPE: PRT
<213> ORGANISM: Homo sapiens

<400> SEQUENCE: 2

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Phe Phe Asp Trp Leu Leu Gly Ser Ala Phe Asp
            100                 105                 110

Ile Trp Gly Gln Gly Thr Thr Val Thr Val Ser Ser
        115                 120

<210> SEQ ID NO 3
<211> LENGTH: 107
<212> TYPE: PRT
<213> ORGANISM: Homo sapiens

<400> SEQUENCE: 3

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Leu
                85                  90                  95

Thr Phe Gly Gly Gly Thr Lys Val Glu Ile Lys
            100                 105

<210> SEQ ID NO 4
<211> LENGTH: 125
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
 50                  55                  60

Gln Gly Arg Val Thr Val Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Arg Asp Asn Trp Asp Pro Tyr Tyr Tyr Tyr Gly Met
            100                 105                 110

Asp Val Trp Gly Gln Gly Thr Thr Val Thr Val Ser Ser
            115                 120                 125

<210> SEQ ID NO 5
<211> LENGTH: 6
<212> TYPE: PRT
<213> ORGANISM: Homo sapiens

<400> SEQUENCE: 5

Gln Gly Ile Arg Asn Asp
1               5

<210> SEQ ID NO 6
<211> LENGTH: 3
<212> TYPE: PRT
<213> ORGANISM: Homo sapiens

<400> SEQUENCE: 6

Ala Ala Ser
1

<210> SEQ ID NO 7
<211> LENGTH: 9
<212> TYPE: PRT
<213> ORGANISM: Homo sapiens

<400> SEQUENCE: 7

Leu Gln Asp Tyr Asn Tyr Pro Arg Thr
1               5

<210> SEQ ID NO 8
<211> LENGTH: 8
<212> TYPE: PRT
<213> ORGANISM: Homo sapiens

<400> SEQUENCE: 8

Gly Phe Thr Phe Ser Ser Tyr Ala
1               5

<210> SEQ ID NO 9
<211> LENGTH: 8
<212> TYPE: PRT
<213> ORGANISM: Homo sapiens

<400> SEQUENCE: 9

Ile Ser Tyr Asp Gly Ser Asn Lys
1               5

<210> SEQ ID NO 10
<211> LENGTH: 17
<212> TYPE: PRT
<213> ORGANISM: Homo sapiens
```

-continued

```
<400> SEQUENCE: 10

Ala Arg Glu Leu Arg Phe Phe Asp Trp Leu Leu Gly Ser Ala Phe Asp
1               5                   10                  15

Ile

<210> SEQ ID NO 11
<211> LENGTH: 6
<212> TYPE: PRT
<213> ORGANISM: Homo sapiens

<400> SEQUENCE: 11

Gln Ser Ile Asn Ser Trp
1               5

<210> SEQ ID NO 12
<211> LENGTH: 3
<212> TYPE: PRT
<213> ORGANISM: Homo sapiens

<400> SEQUENCE: 12

Lys Ala Ser
1

<210> SEQ ID NO 13
<211> LENGTH: 9
<212> TYPE: PRT
<213> ORGANISM: Homo sapiens

<400> SEQUENCE: 13

Gln Gln Tyr Asn Ser Phe Pro Leu Thr
1               5

<210> SEQ ID NO 14
<211> LENGTH: 8
<212> TYPE: PRT
<213> ORGANISM: Homo sapiens

<400> SEQUENCE: 14

Gly Gly Thr Phe Ser Ser Tyr Ala
1               5

<210> SEQ ID NO 15
<211> LENGTH: 8
<212> TYPE: PRT
<213> ORGANISM: Homo sapiens

<400> SEQUENCE: 15

Ile Ile Pro Ile Leu Gly Ile Ala
1               5

<210> SEQ ID NO 16
<211> LENGTH: 18
<212> TYPE: PRT
<213> ORGANISM: Homo sapiens

<400> SEQUENCE: 16

Ala Arg Glu Arg Asp Asn Trp Asp Pro Tyr Tyr Tyr Tyr Gly Met
1               5                   10                  15

Asp Val

<210> SEQ ID NO 17
<211> LENGTH: 330
<212> TYPE: PRT
```

<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 330
<212> TYPE: PRT
<213> ORGANISM: Homo sapiens

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Val Gly Gly Pro Ser Val Phe Leu Leu Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Leu Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Leu Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 448
<212> TYPE: PRT
<213> ORGANISM: Homo sapiens

<400> SEQUENCE: 19

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
 50                  55                  60
```

-continued

```
Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 20
<211> LENGTH: 220
<212> TYPE: PRT
<213> ORGANISM: Homo sapiens

<400> SEQUENCE: 20

-continued

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 21
<211> LENGTH: 21
<212> TYPE: PRT
<213> ORGANISM: Homo sapiens

<400> SEQUENCE: 21

Met Ala Leu Pro Val Thr Ala Leu Leu Leu Pro Leu Ala Leu Leu Leu
1               5                   10                  15

His Ala Ala Arg Pro
            20

<210> SEQ ID NO 22
<211> LENGTH: 49
<212> TYPE: PRT
<213> ORGANISM: Homo sapiens

<400> SEQUENCE: 22

Arg Thr Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
            35                  40                  45

Tyr

<210> SEQ ID NO 23
<211> LENGTH: 22
```

```
<212> TYPE: PRT
<213> ORGANISM: Homo sapiens

<400> SEQUENCE: 23

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 25
<211> LENGTH: 112
<212> TYPE: PRT
<213> ORGANISM: Homo sapiens

<400> SEQUENCE: 25

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 26
<211> LENGTH: 22
<212> TYPE: PRT
<213> ORGANISM: Homo sapiens

<400> SEQUENCE: 26

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 27
<211> LENGTH: 386
<212> TYPE: PRT
<213> ORGANISM: Homo sapiens

<400> SEQUENCE: 27
```

```
Leu Leu Leu Val Thr Ser Leu Leu Leu Cys Glu Leu Pro His Pro Ala
  1               5                  10                  15

Phe Leu Leu Ile Pro Ala Cys Gly Ala Asp Ser Tyr Glu Met Glu Glu
             20                  25                  30

Asp Gly Val Arg Lys Cys Lys Cys Glu Gly Pro Cys Arg Lys Val
             35                  40                  45

Cys Asn Gly Ile Gly Ile Gly Glu Phe Lys Asp Ser Leu Ser Ile Asn
 50                  55                  60

Ala Thr Asn Ile Lys His Phe Lys Asn Cys Thr Ser Ile Ser Gly Asp
 65                  70                  75                  80

Leu His Ile Leu Pro Val Ala Phe Arg Gly Asp Ser Phe Thr His Thr
             85                  90                  95

Pro Pro Leu Asp Pro Gln Glu Leu Asp Ile Leu Lys Thr Val Lys Glu
            100                 105                 110

Ile Thr Gly Phe Leu Leu Ile Gln Ala Trp Pro Glu Asn Arg Thr Asp
            115                 120                 125

Leu His Ala Phe Glu Asn Leu Glu Ile Ile Arg Gly Arg Thr Lys Gln
            130                 135                 140

His Gly Gln Phe Ser Leu Ala Val Val Ser Leu Asn Ile Thr Ser Leu
145                 150                 155                 160

Gly Leu Arg Ser Leu Lys Glu Ile Ser Asp Gly Asp Val Ile Ile Ser
                165                 170                 175

Gly Asn Lys Asn Leu Cys Tyr Ala Asn Thr Ile Asn Trp Lys Lys Leu
                180                 185                 190

Phe Gly Thr Ser Gly Gln Lys Thr Lys Ile Ile Ser Asn Arg Gly Glu
                195                 200                 205

Asn Ser Cys Lys Ala Thr Gly Gln Val Cys His Ala Leu Cys Ser Pro
210                 215                 220

Glu Gly Cys Trp Gly Pro Glu Pro Arg Asp Cys Val Ser Cys Arg Asn
225                 230                 235                 240

Val Ser Arg Gly Arg Glu Cys Val Asp Lys Cys Asn Leu Leu Glu Gly
                245                 250                 255

Glu Pro Arg Glu Phe Val Glu Asn Ser Glu Cys Ile Gln Cys His Pro
            260                 265                 270

Glu Cys Leu Pro Gln Ala Met Asn Ile Thr Cys Thr Gly Arg Gly Pro
            275                 280                 285

Asp Asn Cys Ile Gln Cys Ala His Tyr Ile Asp Gly Pro His Cys Val
            290                 295                 300

Lys Thr Cys Pro Ala Gly Val Met Gly Glu Asn Asn Thr Leu Val Trp
305                 310                 315                 320

Lys Tyr Ala Asp Ala Gly His Val Cys His Leu Cys His Pro Asn Cys
            325                 330                 335

Thr Tyr Gly Cys Thr Gly Pro Gly Leu Glu Gly Cys Pro Thr Asn Gly
            340                 345                 350

Pro Lys Ile Pro Ser Ile Ala Thr Gly Met Val Gly Ala Leu Leu Leu
            355                 360                 365

Leu Leu Val Val Ala Leu Gly Ile Gly Leu Phe Met Arg Arg Arg His
370                 375                 380

Ile Val
385

<210> SEQ ID NO 28
<211> LENGTH: 107
<212> TYPE: PRT
```

<213> ORGANISM: Homo sapiens

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 107
<212> TYPE: PRT
<213> ORGANISM: Homo sapiens

<400> SEQUENCE: 29

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Leu
                85                  90                  95

Thr Phe Gly Gln Gly Thr Lys Val Glu Ile Lys
            100                 105

<210> SEQ ID NO 30
<211> LENGTH: 122
<212> TYPE: PRT
<213> ORGANISM: Homo sapiens

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Val Pro Gly Lys Gly Leu Glu Trp Val
        35                  40                  45

Ala Ile Ile Ser Tyr Asp Gly Ser Ile Lys Tyr Tyr Ala Asp Ser Val
    50                  55                  60

Lys Gly Gln Phe Thr Ile Ser Arg Asp Asn Ser Lys Asn Thr Leu Ser
65                  70                  75                  80

Leu Gln Met Asn Ser Leu Arg Pro Glu Asp Thr Ala Val Tyr Tyr Cys
                85                  90                  95

```
Ala Arg Asp Pro Thr Met Val Arg Gly Val Arg Gly Met Asp Val Trp
            100                 105                 110

Gly Gln Gly Thr Thr Val Thr Val Ser Ser
        115                 120

<210> SEQ ID NO 31
<211> LENGTH: 107
<212> TYPE: PRT
<213> ORGANISM: Homo sapiens

<400> SEQUENCE: 31

Glu Ile Val Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Leu Glu Ile Lys
            100                 105

<210> SEQ ID NO 32
<211> LENGTH: 124
<212> TYPE: PRT
<213> ORGANISM: Homo sapiens

<400> SEQUENCE: 32

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Phe Phe Asp Trp Leu Leu Gly Arg Ala Phe Asp
            100                 105                 110

Ile Trp Gly Gln Gly Thr Met Val Thr Val Ser Ser
        115                 120

<210> SEQ ID NO 33
<211> LENGTH: 107
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Leu Glu Ile Lys
                100                 105
```

<210> SEQ ID NO 34
<211> LENGTH: 107
<212> TYPE: PRT
<213> ORGANISM: Homo sapiens

<400> SEQUENCE: 34

```
Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Leu Glu Ile Lys
                100                 105
```

<210> SEQ ID NO 35
<211> LENGTH: 122
<212> TYPE: PRT
<213> ORGANISM: Homo sapiens

<400> SEQUENCE: 35

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Thr Met Val Arg Gly Val Arg Gly Met Asp Val Trp
                100                 105                 110

Gly Gln Gly Thr Thr Val Thr Val Ser Ser
                115                 120
```

<210> SEQ ID NO 36
<211> LENGTH: 107
<212> TYPE: PRT
<213> ORGANISM: Homo sapiens

<400> SEQUENCE: 36

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Leu Glu Ile Lys
            100                 105

<210> SEQ ID NO 37
<211> LENGTH: 124
<212> TYPE: PRT
<213> ORGANISM: Homo sapiens

<400> SEQUENCE: 37

Gly Ala Ala Thr Ala Val Gly Arg Arg Thr Val Glu Ala Ser Glu Thr
1               5                   10                  15

Leu Ser Leu Thr Cys Ala Val Tyr Gly Gly Ser Phe Ser Gly Tyr Tyr
            20                  25                  30

Trp Ser Trp Ile Arg Gln Pro Pro Gly Lys Gly Leu Glu Trp Ile Gly
        35                  40                  45

Glu Ile Asn His Ser Gly Ser Thr Asn Tyr Asn Pro Ser Leu Lys Ser
    50                  55                  60

Arg Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Gly Pro Tyr Asp Ile Leu Thr Gly Tyr Tyr Pro Tyr Trp Tyr Phe Asp
            100                 105                 110

Leu Trp Gly Arg Gly Thr Leu Val Thr Val Ser Ser
        115                 120

<210> SEQ ID NO 38
<211> LENGTH: 107
<212> TYPE: PRT
<213> ORGANISM: Homo sapiens

<400> SEQUENCE: 38

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Val Glu Ile Lys
                100                 105
```

<210> SEQ ID NO 39
<211> LENGTH: 119
<212> TYPE: PRT
<213> ORGANISM: Homo sapiens

<400> SEQUENCE: 39

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Pro Val Arg Gly Phe Asp Tyr Trp Gly Gln Gly
                100                 105                 110

Thr Leu Val Thr Val Ser Ser
            115
```

<210> SEQ ID NO 40
<211> LENGTH: 107
<212> TYPE: PRT
<213> ORGANISM: Homo sapiens

<400> SEQUENCE: 40

```
Glu Ile Val Met Thr Gln Ser Pro Ser Thr Leu Ser Ala Ser Ile Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Val Glu Ile Lys
                100                 105
```

<210> SEQ ID NO 41
<211> LENGTH: 122
<212> TYPE: PRT
<213> ORGANISM: Homo sapiens

<400> SEQUENCE: 41

-continued

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Met Val Arg Gly Val Arg Gly Met Asp Val Trp
            100                 105                 110

Gly Gln Gly Thr Thr Val Thr Val Ser Ser
            115                 120
```

<210> SEQ ID NO 42
<211> LENGTH: 113
<212> TYPE: PRT
<213> ORGANISM: Homo sapiens

<400> SEQUENCE: 42

```
Glu Thr Thr Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Gln Gln
                85                  90                  95

Tyr Tyr Ser Thr Pro Tyr Thr Phe Gly Gln Gly Thr Lys Val Asp Ile
            100                 105                 110

Lys
```

<210> SEQ ID NO 43
<211> LENGTH: 126
<212> TYPE: PRT
<213> ORGANISM: Homo sapiens

<400> SEQUENCE: 43

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Asp Met His Trp Val Arg Gln Ala Pro Gly Lys Gly Leu Glu Trp Val
        35                  40                  45

Ala Asp Ile Ser Asp Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Ala Ala Val Tyr Tyr Cys
                 85                  90                  95

Ala Arg Glu Gly Leu Arg Trp Phe Gly Glu Phe Tyr Tyr Ser Tyr Gly
            100                 105                 110

Met Asp Val Trp Gly Gln Gly Thr Thr Val Thr Val Ser Ser
        115                 120                 125

<210> SEQ ID NO 44
<211> LENGTH: 113
<212> TYPE: PRT
<213> ORGANISM: Homo sapiens

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Asp Ser Thr Pro Tyr Thr Phe Gly Gln Gly Thr Lys Leu Glu Ile
            100                 105                 110

Lys

<210> SEQ ID NO 45
<211> LENGTH: 126
<212> TYPE: PRT
<213> ORGANISM: Homo sapiens

<400> SEQUENCE: 45

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Asp Ile Ser Asp Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Glu Gly Leu Arg Trp Phe Gly Glu Phe Tyr Tyr Ser Tyr Gly
            100                 105                 110

Met Asp Val Trp Gly Gln Gly Thr Thr Val Thr Val Ser Ser
        115                 120                 125

<210> SEQ ID NO 46
<211> LENGTH: 15
<212> TYPE: PRT
<213> ORGANISM: Artificial Sequence
<220> FEATURE:
<223> OTHER INFORMATION: The sequence is artificially synthesized

```
<400> SEQUENCE: 46

Gly Gly Gly Gly Ser Gly Gly Gly Gly Ser Gly Gly Gly Gly Ser
1               5                   10                  15
```

ANTIBODY OR CHIMERIC ANTIGEN RECEPTOR WHICH TARGETS CLAUDIN 18.2

CROSS-REFERENCE TO RELATED APPLICATIONS

This application is a National Stage application under 35 U.S.C. § 371 of International Application No. PCT/CN2020/092849, filed on May 28, 2020, which claims the benefit of Chinese Application No. 2019-10459622.3, filed on May 30, 2019, and Chinese application No. 201910459129.1, filed May 30, 2019, the contents of which are hereby incorporated by reference in their entirety.

SEQUENCE LISTING

This application contains a Sequence Listing that has been submitted electronically as an TXT file named 48644-0004US1_ST25.TXT. The TXT file, created on Feb. 7, 2025, is 43,263 bytes in size. The material in the TXT file is hereby incorporated by reference in its entirety.

TECHNICAL FIELD

The present invention relates to the technical field of biomedicine or biopharmaceuticals, and specifically, relates to an antibody or an antigen-binding fragment thereof, or a chimeric antigen receptor that targets Claudin18.2, as well as a preparation method and use of the same for preparing a pharmaceutical composition, treating, preventing, detecting or diagnosing a disease.

BACKGROUND

Claudin18.2 is transiently expressed in gastric epithelial cells only, and is seldom expressed in other normal tissues. However, the expression of Claudin18.2 is abnormally elevated in many cancerous tissues (Niimi, *Mol. Cell Biol.*, 21:7380-90, 2001). Claudin18.2 is expressed in gastric cancer, esophageal cancer, pancreatic cancer, lung cancer, ovarian cancer and other tumors. Antibodies targeting Claudin 18.2 can mediate specific lysis of tumor cells through ADCC, CDC, inducing apoptosis and direct inhibition of proliferation. Therefore, Claudin18.2 is currently the most promising target in treatment of gastric cancer, esophageal cancer, pancreatic cancer, lung cancer and ovarian cancer.

Claudin18.1 is selectively expressed in epithelial cells of normal lungs and stomachs. The presence of two different variants introduces more complexity to Claudin18 molecules (Niimi, *Mol. Cell Biol.*, 21:7380-90, 2001). How to further improve the effectiveness and safety is an issue to be considered in the field.

IMAB362 developed by Ganymed (Chinese Patent No. CN201380026898.3) is one of the first Claudin18.2 antibodies put into clinical trials. In its Phase II clinical trials for gastric cancer, the antibody used in combination with chemotherapy significantly prolonged the survival (13.2 vs. 8.4 months) compared with standard chemotherapy, and had more significant efficacy and a longer median survival time (16.7 months) in patients with high expression of Claudin18.2 (NCT01630083).

The present invention provides an antibody or an antigen-binding fragment thereof, or a chimeric antigen receptor T cell that targets Claudin18.2 with good efficacy for Claudin18.2-positive tumors, bringing new hope to patients with advanced gastric cancer, pancreatic cancer, and the like.

SUMMARY

All embodiments concerning VL (light chain variable region), VH (heavy chain variable region), LCDR (light chain complementarity determining region), HCDR (heavy chain complementarity determining region), LCDR1, LCDR2, LCDR3, HCDR1, HCDR2, and HCDR3 throughout the present invention may be implemented alone or in any combination.

In one aspect, the present invention provides an antibody or an antigen-binding fragment thereof, wherein:
in some embodiments, the antibody or the antigen-binding fragment thereof comprises any of the following combinations:
(1) three light chain complementarity determining regions comprising an LCDR1 amino acid sequence set forth in SEQ ID NO: 5, an LCDR2 amino acid sequence set forth in SEQ ID NO: 6 and an LCDR3 amino acid sequence set forth in SEQ ID NO: 7, and/or three heavy chain complementarity determining regions comprising an HCDR1 amino acid sequence set forth in SEQ ID NO: 8, an HCDR2 amino acid sequence set forth in SEQ ID NO: 9 and an HCDR3 amino acid sequence set forth in SEQ ID NO: 10;
(2) three light chain complementarity determining regions comprising an LCDR1 amino acid sequence set forth in SEQ ID NO: 11, an LCDR2 amino acid sequence set forth in SEQ ID NO: 12 and an LCDR3 amino acid sequence set forth in SEQ ID NO: 13, and/or three heavy chain complementarity determining regions comprising an HCDR1 amino acid sequence set forth in SEQ ID NO: 14, an HCDR2 amino acid sequence set forth in SEQ ID NO: 15 and an HCDR3 amino acid sequence set forth in SEQ ID NO: 16;
in some embodiments, the antibody or the antigen-binding fragment thereof comprises any of the following combinations:
(1) a light chain variable region of an amino acid sequence set forth in SEQ ID NO: 1 and/or a heavy chain variable region of an amino acid sequence set forth in SEQ ID NO: 2;
(2) a light chain variable region of an amino acid sequence set forth in SEQ ID NO: 3 and/or a heavy chain variable region of an amino acid sequence set forth in SEQ ID NO: 4.

In one aspect of the present invention, the antibody or the antigen-binding fragment thereof includes monoclonal antibodies, polyclonal antibodies, chimeric antibodies, humanized antibodies, Fab, Fab', F(ab')$_2$, Fv, scFv or dsFv fragments.

In one aspect of the present invention, the antibody or the antigen-binding fragment thereof comprises a heavy chain constant region of an amino acid sequence set forth in SEQ ID NO: 17.

In one aspect of the present invention, the antibody or the antigen-binding fragment thereof comprises a heavy chain constant region of an amino acid sequence set forth in SEQ ID NO: 18.

In one aspect of the present invention, the antibody or the antigen-binding fragment thereof comprises a light chain constant region of an amino acid sequence set forth in SEQ ID NO: 28.

The antibody or the antigen-binding fragment disclosed herein has one or more of the following advantages: higher affinity to cells expressing Claudin18.2, enhanced ability to mediate ADCC, and better tumor inhibitory effect.

In one aspect of the present invention, any of the above antibodies or the antigen-binding fragments thereof binds to Claudin18.2.

The present invention also relates to a chimeric antigen receptor comprising the antibody or the antigen-binding fragment thereof, a related CAR-T cell, and a preparation method and use of the same.

Specifically, in one aspect, the present invention relates to a chimeric antigen receptor (CAR) comprising any of the above antibodies or the antigen-binding fragments thereof, wherein three light chain complementarity determining regions of the antibody or the antigen-binding fragment thereof comprise an LCDR1 amino acid sequence set forth in SEQ ID NO: 5, an LCDR2 amino acid sequence set forth in SEQ ID NO: 6 and an LCDR3 amino acid sequence set forth in SEQ ID NO: 7; and three heavy chain complementarity determining regions of the antibody or the antigen-binding fragment thereof comprise an HCDR1 amino acid sequence set forth in SEQ ID NO: 8, an HCDR2 amino acid sequence set forth in SEQ ID NO: 9 and an HCDR3 amino acid sequence set forth in SEQ ID NO: 10.

In another aspect, the present invention relates to a chimeric antigen receptor (CAR) comprising an antibody or an antigen-binding fragment thereof, wherein three light chain complementarity determining regions of the antibody or the antigen-binding fragment thereof comprise an LCDR1 amino acid sequence set forth in SEQ ID NO: 11, an LCDR2 amino acid sequence set forth in SEQ ID NO: 12 and an LCDR3 amino acid sequence set forth in SEQ ID NO: 13; and three heavy chain complementarity determining regions of the antibody or the antigen-binding fragment thereof comprise an HCDR1 amino acid sequence set forth in SEQ ID NO: 14, an HCDR2 amino acid sequence set forth in SEQ ID NO: 15 and an HCDR3 amino acid sequence set forth in SEQ ID NO: 16.

In another aspect, the present invention relates to a chimeric antigen receptor, wherein the sequence of the VL of the antibody or the antigen-binding fragment thereof is SEQ ID NO: 1, and the sequence of the VH is SEQ ID NO: 2.

In another aspect, the present invention relates to a chimeric antigen receptor, wherein the sequence of the VL of the antibody or the antigen-binding fragment thereof is SEQ ID NO: 3, and the sequence of the VH is SEQ ID NO: 4.

In another aspect, the VH and the VL of the antibody or the antigen-binding fragment thereof are linked through a linker; preferably, through a GGGGSGGGGSGGGGS (SEQ ID NO: 46) linker; preferably, in the order of VH-GGGGSGGGGSGGGGS-VL (SEQ ID NO: 46) from N terminus to C terminus.

In another aspect, the present invention relates to a chimeric antigen receptor which sequentially comprises the antibody or the antigen-binding fragment thereof according to any of the preceding aspects, an extracellular hinge region, a transmembrane region and an intracellular signaling region.

In another aspect, the present invention relates to a chimeric antigen receptor, of which the antibody or the antigen-binding fragment thereof is directed by a signal peptide.

In another aspect, the present invention relates to a chimeric antigen receptor, wherein the signal peptide may be a CD8a signal peptide, a VH3 signal peptide, an IL2 signal peptide or the like, the extracellular hinge region may be a CD8 hinge region, a CD28 hinge region or the like, the transmembrane region may be a CD8 transmembrane region, a CD28 transmembrane region, a 4-1BB transmembrane region or the like, and the intracellular signaling region may be a CD28 signaling region, a 4-1BB signaling region, an OX40 signaling region, a CD3ζ C. signaling region or the like.

In another aspect, the present invention relates to a chimeric antigen receptor, wherein the extracellular hinge region is a CD8 hinge region, the transmembrane region is a CD8 transmembrane region, the intracellular signaling region is 4-1BB and CD3ζ, and the antibody or the antigen-binding fragment thereof is directed by a CD8α signal peptide. Preferably, the CD8α signal peptide is a CD8a signal peptide set forth in SEQ ID NO: 21, the extracellular hinge region is a CD8 hinge region set forth in SEQ ID NO: 22, the transmembrane region is a CD8 transmembrane region set forth in SEQ ID NO: 23, and the intracellular signaling region is 4-1BB set forth in SEQ ID NO: 24 and CD3ζ set forth in SEQ ID NO: 25.

In another aspect, the present invention relates to a nucleic acid encoding the antibody or the antigen-binding fragment thereof, or the chimeric antigen receptor according to any of the preceding aspects.

In another aspect, the present invention relates to a vector comprising the nucleic acid according to the previous aspect, or expressing the antibody or the antigen-binding fragment thereof or the chimeric antigen receptor according to any of the preceding aspects. Preferably, the vector may be a viral vector; preferably, the viral vector includes, but is not limited to, a lentivirus vector, an adenovirus vector, an adeno-associated virus vector or a retrovirus vector; preferably, the vector may be a non-viral vector; preferably, the non-viral vector may be a transposon vector; preferably, the transposon vector may be a Sleeping Beauty vector, a Piggy Bac vector, or the like; preferably, the vector may be a mammalian expression vector; preferably, the expression vector may be a bacterial expression vector; preferably, the expression vector may be a fungal expression vector.

In another aspect, the vector is a lentivirus vector.

In another aspect, the lentivirus vector is plasmid pRRLSIN-Claudin18.2CAR-P2A-EGFRt shown in FIG. 11.

In another aspect, the vector is a PiggyBac (PB) transposon vector.

In another aspect, the PB transposon vector is plasmid PB CN02 CAR shown in FIG. 24.

In another aspect, the present invention relates to a cell expressing the antibody or the antigen-binding fragment thereof or the chimeric antigen receptor according to any of the preceding aspects. Preferably, the cell is a bacterial cell; preferably, the bacterial cell is an *Escherichia coli* cell or the like; preferably, the cell is a fungal cell; preferably, the fungal cell is a yeast cell; preferably, the yeast cell is a *Pichia pastoris* cell or the like; preferably, the cell is a mammalian cell; and preferably, the mammalian cell is a Chinese hamster ovary (CHO) cell, a human embryonic kidney cell (293), a B cell, a T cell, a DC cell, a NK cell, or the like.

In another aspect, the present invention relates to a CAR-T cell comprising the chimeric antigen receptor according to any of the preceding aspects.

In another aspect, the present invention relates to a method for preparing the CAR-T cell according to the previous aspect, comprising transfecting a T cell with a vector comprising a nucleic acid encoding the chimeric antigen receptor according to any of the preceding aspects. In a preferred embodiment, the vector is a non-viral vector.

In a preferred embodiment, the vector is a PB transposon vector. In a preferred embodiment, the PB transposon vector is plasmid PB CN02 CAR shown in FIG. 24.

In another aspect, the present invention relates to a method for preparing the CAR-T cell according to the previous aspect, comprising transfecting a T cell with a vector comprising a nucleic acid encoding a transposase. In another preferred embodiment, the transposase is PB transposase.

In another aspect, the present invention relates to a method for preparing the CAR-T cell according to the previous aspect, comprising transfecting a T cell with a transposon vector comprising a nucleic acid encoding the chimeric antigen receptor according to any of the preceding aspects and a transposase vector comprising a nucleic acid encoding a transposase. In a preferred embodiment, the transposon vector is a PB transposon vector. In a preferred embodiment, the PB transposon vector is plasmid PB CN02 CAR shown in FIG. 24. In a preferred embodiment, the transposase is PB transposase.

In another aspect, the present invention relates to a method for preparing the CAR-T cell according to the previous aspect, comprising transducing a T cell with a lentivirus comprising the chimeric antigen receptor vector according to any of the preceding aspects to give the CAR-T cell.

In another aspect, the present invention relates to a pharmaceutical composition comprising the CAR-T cell according to any of the preceding aspects.

In another aspect, the present invention relates to a method for treating cancer, comprising administering the CAR-T cell according to any of the preceding aspects to a subject in need.

In another aspect, the present invention relates to use of the CAR-T cell according to any of the preceding aspects in treating cancer.

In another aspect, the present invention relates to use of the CAR-T cell according to any of the preceding aspects in preparing a pharmaceutical composition for treating cancer.

In another aspect, the present invention relates to a CAR-T cell having one or more of the following advantages: good killing ability to cells expressing Claudin18.2; and low killing ability to cells expressing Claudin18.1.

In one aspect, the present invention provides a pharmaceutical composition comprising: the antibody or the antigen-binding fragment thereof, the chimeric antigen receptor, the nucleic acid encoding the same, or the cell expressing the same disclosed herein; and a pharmaceutically acceptable carrier. The pharmaceutically acceptable carrier includes one or more of the following: pharmaceutically acceptable vehicle, disperser, additive, plasticizer, and excipient.

In one aspect, the present invention provides a kit comprising the antibody or the antigen-binding fragment thereof, a chimeric antigen receptor, or the nucleic acid encoding the same disclosed herein.

In some embodiments, the pharmaceutical composition may also comprise other therapeutic agents. In some embodiments, other therapeutic agents include chemotherapeutic agents, immunotherapeutic agents, or hormone therapeutic agents. The antibody or the antigen-binding fragment can be used in combination with other therapeutic agents to enhance the efficacy.

In some embodiments, "to enhance the efficacy" refers to enhancing the efficacy of other therapeutic agents or modalities. The antibody or the antigen-binding fragment disclosed herein can be administered alone or in combination with other therapeutic agents or modalities. In some embodiments, other therapeutic agents or modalities include chemotherapeutic agents, immunotherapeutic agents, hormone therapeutic agents, radiotherapy and surgery.

In another aspect, the present invention relates to use of the antibody or the antigen-binding fragment thereof, the chimeric antigen receptor, the nucleic acid, the vector or the cell according to any of the preceding aspects in preparing a pharmaceutical composition for treating or preventing a disease.

In another aspect, the present invention relates to use of the antibody or the antigen-binding fragment thereof, the chimeric antigen receptor, or the nucleic acid according to any of the preceding aspects in preparing a kit for diagnosis or detection.

In another aspect, a method for treating or preventing a disease is provided, comprising administering the antibody or the antigen-binding fragment, the chimeric antigen receptor, the nucleic acid, the vector, the cell, or the pharmaceutical composition disclosed herein to a subject in need.

In another aspect, a method for diagnosis or detection is provided, comprising administering the antibody or the antigen-binding fragment, the chimeric antigen receptor, the nucleic acid, or the kit disclosed herein to a subject in need or a sample.

In another aspect, the present invention provides use of the antibody or the antigen-binding fragment thereof, the chimeric antigen receptor, the nucleic acid, the vector, the cell, or the pharmaceutical composition according to any of the preceding aspects for treating or preventing a disease.

In another aspect, the present invention provides use of the antibody or the antigen-binding fragment thereof, the chimeric antigen receptor, the nucleic acid, or the kit according to any of the preceding aspects for detection or diagnosis.

In another aspect, the disease is a cancer.

In another aspect, the cancer is a Claudin18.2-positive cancer.

In another aspect, the cancer includes gastric cancer, pancreatic cancer, esophageal cancer, lung cancer, ovarian cancer, head and neck cancer, bladder cancer, cervical cancer, sarcoma, cytoma, colon cancer, kidney cancer, colorectal cancer, liver cancer, melanoma, breast cancer, myeloma, neuroglioma, leukemia, lymphoma, and the like.

DRAWINGS

DETAILED DESCRIPTION

Figure 1:
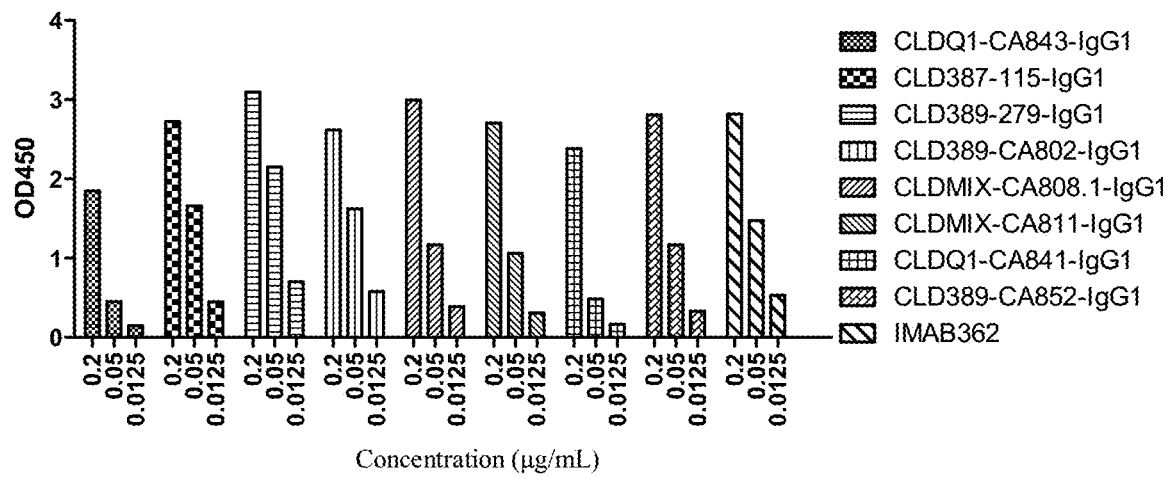
FIGS. 1-2 show the binding sensitivity of candidate antibodies to Claudin18.2 protein measured by ELISA.

The present invention will be further described in conjunction with the following specific examples. The examples described herein are only some examples of the present invention, but not all examples. It should be understood that the following examples are given to provide those of ordinary skill in the art a complete disclosure and description of how to utilize the methods and the compositions, but are not intended to limit the scope of the present invention. Based on the examples of the present invention, all other examples obtained by those of ordinary skill in the art without creative work shall fall within the protection scope of the present invention.

1 Example 1. Production of Anti-Claudin18.2 Monoclonal Antibody 1.1 Immunization BoAn-hMab transgenic mice from Shandong BoAn Biotechnology Co. Ltd. (prepared according to the method described in Chinese Patent No. CN103571872B) were immunized with plasmids (KYinno) containing Claudin18.2 genes and CHO cells (KYinno) stably expressing Claudin18.2 protein. Plasmids were used for the first immunization, and the second to the seventh immunizations were conducted using plasmids and cells alternately. A total of 10 mice were immunized. Five mice with higher serum concentration were selected for booster immunization, and the mice were euthanized 4 days later. Spleens were processed and frozen for later use.

1.2 Construction of Phage Library

Spleen cells of the immunized mice were added with Trizol (Thermo Scientific, catalog number: 15596-026) for complete lysis, and then added with a 1/5 volume of chloroform and mixed well. The mixture was incubated at room temperature for 20 min, and centrifuged at 12000 rpm at 4° C. for 20 min. The supernatant was added with an equal volume of isopropanol. The resulting mixture was incubated at room temperature for 20 min and then centrifuged at 12000 rpm at 4° C. for 20 min. The supernatant was discarded, and the precipitate was washed with 75% ethanol twice and then centrifuged at 12000 rpm at 4° C. for 5 min. The supernatant was discarded, and the precipitate was dried at room temperature and then resuspended with DEPC water to give RNA, which was then reversely transcribed into cDNA using a Roche reverse transcription kit Transcriptor First Strand cDNA Synthesis Kit as per the instructions (Roche Applied Science, catalog number: 4897030001).

The phage library was constructed by the method described in Carlos F. Barbas III, *Phage display: A Laboratory Manual*. Sequences of variable regions of heavy and light chains were obtained from cDNA by PCR, and then subjected to overlap extension PCR to give scFv sequence. Then, the scFv was digested with SfiI enzyme (NEB, catalog number: R0123L) for 5 h (50° C.) and ligated with plasmid pCOMB3x (Biovector Science Lab, Inc., BIOVECTOR510837) through T4 DNA ligase (Sino Biological Inc.). The ligation product was electrotransfected into competent *Escherichia coli* TGI cells (Lucigen, catalog number: A96595-2), which were then cultivated on a shaker at 220 rpm at 37° C. and infected with a phage, and the supernatant of the culture was collected, concentrated and purified to give the phage library.

1.3 Screening 1.3.1 Plate screening: A plate was coated with Claudin18.2 protein (Genscript Biotech) at 0.3 μg/well, and incubated overnight at 4° C. The plate was blocked with 2% BSA for 1 h the next day, and the phage library ($2\times10^{12}$) was added for a 2-h incubation. After 4-10 washings, the phages specifically binding to Claudin18.2 were eluted with an eluent buffer (pH 2.2) (4.2 mL of concentrated hydrochloric acid (Tianjin Kemiou Chemical Reagent Co., Ltd.) was added to 500 mL of ultrapure water, and the mixture was adjusted to pH 2.2 with glycine powder (Biotopped, BG0617-500)).

1.3.2 Cell screening: The phage library ($2\times10^{12}$) was rotationally mixed with 293T-Claudin18.1 cells ($3\times 10^6$ cells/vial) at room temperature and incubated for 1 h. The resulting mixture was blocked with 2% BSA for 1 h, then rotationally mixed with 293T-Claudin18.2 cells ($2\times 10^6$ cells/vial) at room temperature and incubated for 2 h. After 4-10 washings, the phages specifically binding to Claudin18.2 were eluted with an eluent buffer (pH 2.2). Phages passing the cell screening could be further screened on plates.

2 Example 2. Construction and Production of Complete Antibodies

Clones CLD387-C115, CLD389-C279\CA802\CA852, CLDQMix-CA808.1\CA811\CA818, CLDQ1-CA841\CA843, CLD393-C1002\C1024 were sequenced by Invitrogen Biotechnology Co., Ltd. The amino acid sequences of the variable regions of the clones are shown in Table 1.

TABLE 1

Amino acid sequences of variable regions of active clones

| Clone ID | VL sequence | VH sequence |
|---|---|---|
| CA808.1 | DIVMTQSPSSLSASVGDRVTITCRASQGIRNDLGWYQQKPGKAPKLLIYAASSLQSGVPSRFSGSGSGTDFTLTISSLQPEDFATYYCLQDYNYPRTFGQGTKVEIK (SEQ ID NO: 1)<br>CDR<br>LCDR1: QGIRND (SEQ ID NO: 5)<br>LCDR2: AAS (SEQ ID NO: 6)<br>LCDR3: LQDYNYPRT (SEQ ID NO: 7) | EVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARELRFFDWLLGSAFDIWGQGTTVTVSS (SEQ ID NO: 2)<br>CDR<br>HCDR1: GFTFSSYA (SEQ ID NO: 8)<br>HCDR2: ISYDGSNK (SEQ ID NO: 9)<br>HCDR3: ARELRFFDWLLGSAFDI (SEQ ID NO: 10) |
| CA841 | DIQMTQSPSTLSASVGDRVTITCRASQSINSWLAWYQQKPGKAPKLLIYKASSLESGVPSRFSGSGSGTEFTLTISSLQPDDFATYYCQQYNSFPLTFGGGTKVEIK (SEQ ID NO: 3)<br>CDR<br>LCDR1: QSINSW (SEQ ID NO: 11)<br>LCDR2: KAS (SEQ ID NO: 12)<br>LCDR3: QQYNSFPLT (SEQ ID NO: 13) | QVQLVQSGAEVKKPGSSVKVSCKASGGTFSSYAISWVRQAPGQGLEWMGRIIPILGIANYAQKFQGRVTVTADKSTSTAYMELSSLRSEDTAVYYCARERDNWDPYYYYGMDVWGQGTTVTVSS (SEQ ID NO: 4)<br>CDR<br>HCDR1: GGTFSSYA (SEQ ID NO: 14)<br>HCDR2: IIPILGIA (SEQ ID NO: 15)<br>HCDR3: ARERDNWDPYYYYGMDV (SEQ ID NO: 16) |
| C115 | DIVMTQSPSSLSASVGDRVTITCRASQGIRNDLGWYQQKPGKAPKLLIYAASSLQSGVPSRFSGSGSGTDFTLTISSLQPEDFATYYCLQDYNFPLTFGQGTKVEIK | QVQLVESGGGVVQPGRSLRLSCAASGFTFSSYAMHWVRQVPGKGLEWVAISYDGSIKYYADSVKGQFTISRDNSKNTLSLQMNSLRPEDTAVYYCARDPTMVRGVRGMDVWGQGTTVTVSS |
| C279 | EIVMTQSPPSLSASVGDRVTITCRASQGIRNDLGWYQQKPGKAPKLLIYAASSLQSGVPSRFSGSGSGTDFTLTISSLQPEDFATYYCLQDYNYPWTFGQGTKLEIK | EVQLVQSGGGVVQPGRSLRLSCAASGFTFSNYAMHWVRQAPGKGLEWVAVISYDGSNKYYADSVKGRFTISRDNSKNTLYLQMNSLRAEDTAVYYCARELRFFDWLLGRAFDIWGQGTMVTVSS |
| CA802 | DIQMTQSPSSLSASVGDRVTITCRASQGIRNDLGWYQQKPGKAPKLLIYAASSLQSGVPSRFSGSGSGTDFTLTISSLQPEDFATYYCLQDYNYPLTFGGGTKLEIK | QVQLVESGGGVVQPGRSLRLSCAASGFTFSSYAMHWVRQVPGKGLEWVAISYDGSIKYYADSVKGQFTISRDNSKNTLSLQMNSLRPEDTAVYYCARDPTMVRGVRGMDVWGQGTTVTVSS |
| CA811 | DIVMTQSPSSLSASVGDRVTITCRASQGIRNDLGWYQQKPGKAPKLLIYKASSLESGVPSRFSGSGSGTDFTLTISSLQPEDFATYYCLQDYNYPLTFGGGTKLEIK | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARDPTMVRGVRGMDVWGQGTTVTVSS |
| CA818 | DIVMTQSPSTLSASVGDRVTITCRASQGIRNDLGWYQQKPGKAPKLLIYDASSLQSGVPSRFSGSGYGTDFTLTISSLQPEDFATYYCLQDYNYPWTFGQGTKLEIK | GAATAVGRRTVEASETLSLTCAVYGGSFSGYYWSWIRQPPGKGLEWIGEIHSGSTNYNPSLKSRVTISVDTSKNQFSLKLSSVTAADTAVYYCARGPYDILTGYYPYWYFDLWGRGTLVTVSS |
| CA843 | DIVMTQSPSSLSASVGDRVTITCRASQGIRNDLGWYQQKPGKAPKLLIYAASSLQSGVPSRFSGSGSGTDFTLTISSLQPEDFATYYCLQDYNYPLTFGGGTKVEIK | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAREGIPVRGFDYWGQGTLVTVSS |
| CA852 | EIVMTQSPSTLSASIGDRVTITCRASQGIRNDLGWYQQKPGKAPKLLIYAASSLQSGVPSRFSGSGSGTDFTLTISSLQPEDFATYYCLQDYNYPLTFGGGTKVEIK | QVQLVESGGGVVQPGRSLRLSCAASGFTFSSYAMHWVRQAPGKGLEWVAVISYDGSKKYYADSVKGRFTISRDNSKNTLYLQMNSLRAEDTAVYYCARDPTMVRGVRGMDVWGQGTTVTVSS |
| C1002 | ETTLTQSPDSLAVSLGERATINCKSSQSVLYSSNNKNYLAWYQQKPGQPPKLLIYWASTRESGVPDRFSGSGSGTDFTLTISSLQTEDVAVYYCQQYYSTPYTFGQGTKVDIKVSS | QVQLVESGGGVVQPGRSLRLSCAASGFTFSSHDMHWVRQAPGKGLEWVADISDDGSNKYADSVKGRFTISRDNSKNTLYLQMNSLRAEDAAVYYCAREGLRWFGEFYYSYGMDVWGQGTTVT |
| C1024 | DIVMTQSPDSLAVSLGERATINCKSSQSVLYSSNNKNYLAWYQQKPGQPPKLLIYWASTRESGVPDRFSGSGS | EVQLVQSGGGVVQPGRSLRLSCAASGFTFSSYDMHWVRQAPGKGLEWVADISDDGSNKYADSVKGRFTISRDNS |

TABLE 1-continued

Amino acid sequences of variable regions of active clones

| Clone ID | VL sequence | VH sequence |
|---|---|---|
| | GTDFTLTISSLQAEDVAVYYC<u>QQY</u><br><u>DSTPYT</u>FGQGTKLEIK | KNTLYLQMNSLRAEDAAVYYC<u>ARE</u><br><u>GLRWFGEFYYSYGMD</u>VWGQGTTVT<br>VSS |

Through methods such as variable region gene amplification (2*Phanta Max Master Mix, manufacturer: Vazyme, catalog number: P515-AA, batch number: 7E211 GB), signal peptide and variable region overlap extension, and homologous recombination (ClonExpress II One Step Cloning Kit, manufacturer: Vazyme, catalog number: C112-01, batch number: 7E211L8), nucleotide sequence fragments encoding VH or VL were respectively inserted into vectors pCDNA3.4 (Life Technology) containing a nucleotide sequence encoding a heavy chain constant region (SEQ ID NO: 17) and pCDNA3.4 (Life Technology) containing a nucleotide sequence encoding a light chain constant region (SEQ ID NO: 28). Then the vectors were transfected into HEK293 cells and incubated on a shaker at 37° C./8% $CO_2$/125 rpm. After 6-7 days of transient expression the supernatant was purified by Protein A affinity chromatography to give Claudin18.2 antibodies, and the antibody concentration was determined by the extinction coefficient at UV280.

Antibody IMAB362 was selected as the reference antibody. In the Phase II clinical trial for gastric cancer, the antibody in combination with chemotherapy significantly prolonged the survival (13.2 vs. 8.4 months) as compared with standard chemotherapy. IMAB362 had more significant efficacy and a longer median survival time (16.7 months) in patients with high expression of Claudin18.2. IMAB362 is also one of the first Claudin18.2 antibodies put into clinical trials.

Production of reference antibody: Amino acid sequence of Claudin18.2 antibody IMAB362 of Ganymed is available in IMGT database and the Patent No. CN201380026898, with the heavy chain and light chain sequences set forth in SEQ ID NOs: 19 and 20, respectively. The whole gene sequence was synthesized, inserted in vector pCDNA3.4 and expressed in HEK293 cells to produce an antibody named IMAB362.

Figure 2:
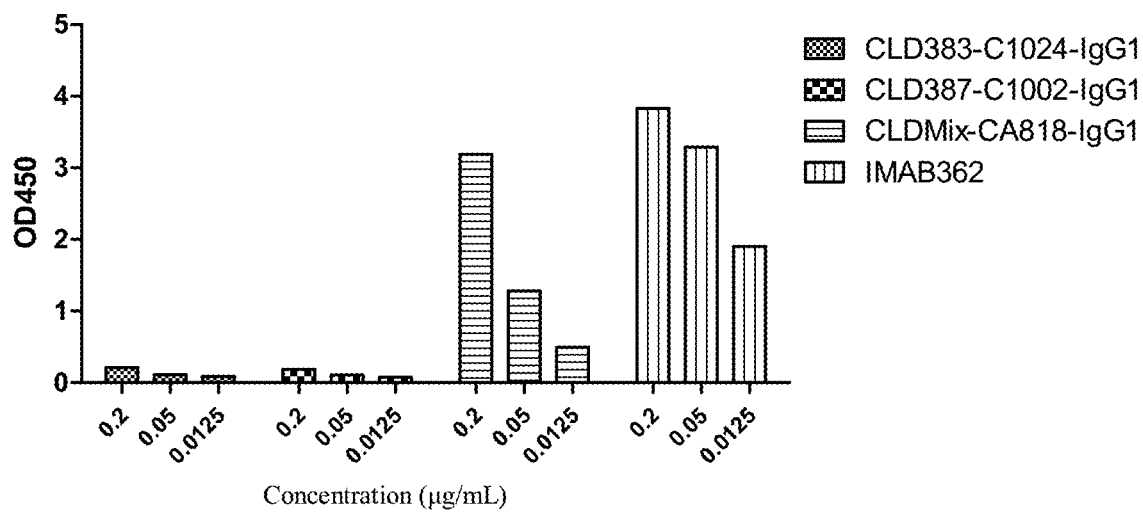

3 Example 3. Characterization of Anti-Claudin18.2 Antibodies 4 3.1 Binding of Antibodies to Claudin18.2 Protein by ELISA Plates were coated with Claudin 18.2 antigen (Genscript Biotech) of different concentrations (0.2 μg/mL, 0.05 μg/mL, 0.0125 μg/mL) at 100 μL/well, incubated overnight at 4° C., and blocked with 3% skimmed milk powder at 37° C. for 1 h. 100 μL of candidate antibodies was added to each well at 1 μg/mL, and incubated at 37° C. for 1 h, followed by goat anti-human IgG/HRP and a 1-h incubation at 37° C. After a 10-min color development, $OD_{450}$ was measured on a microplate reader. The results are shown in FIG. 1, FIG. 2, Table 2 and Table 3.

TABLE 2

Binding sensitivity of candidate antibodies to Claudin18.2 protein measured by ELSIA

| Antibody ID | Antigen concentration (0.2 μg/mL) | Antigen concentration (0.05 μg/mL) | Antigen concentration (0.0125 μg/mL) |
|---|---|---|---|
| CLDQ1-CA843-IgG1 | 1.847 | 0.452 | 0.148 |
| CLD387-115-IgG1 | 2.724 | 1.66 | 0.449 |
| CLD389-279-IgG1 | 3.094 | 2.15 | 0.702 |
| CLD389-CA802-IgG1 | 2.618 | 1.622 | 0.579 |
| CLDMIX-CA808.1-IgG1 | 2.996 | 1.167 | 0.389 |
| CLDMIX-CA811-IgG1 | 2.705 | 1.062 | 0.307 |
| CLDQ1-CA841-IgG1 | 2.38 | 0.484 | 0.165 |
| CLD389-CA852-IgG1 | 2.809 | 1.17 | 0.332 |
| IMAB362 | 2.819 | 1.475 | 0.532 |

TABLE 3

Binding sensitivity of candidate antibodies to Claudin18.2 protein measured by ELSIA

| Antibody ID | Antigen concentration (0.2 μg/mL) | Antigen concentration (0.05 μg/mL) | Antigen concentration (0.0125 μg/mL) |
|---|---|---|---|
| CLD383-C1024-IgG1 | 0.212 | 0.109 | 0.084 |
| CLD387-C1002-IgG1 | 0.187 | 0.105 | 0.076 |
| CLDMix-CA818-IgG1 | 3.189 | 1.281 | 0.492 |
| IMAB362 | 3.832 | 3.288 | 1.901 |

5 3.2 Binding of Antibodies to 293T-Claudin18.1/18.2 Cells and NUGC4 Cells Measured by Flow Cytometry To a 96-well round-bottom plate, 50 μL of 293T-Claudin18.1 or 18.2 cells (KYinno) or NUGC4 cells were added at $1×10^5$ cells/well. Each candidate antibody was serially diluted with FACS buffer (sterile PBS, 0.2% BSA), and added to the 96-well round-bottom plate at 50 μL/well before an incubation at 4° C. for 1 h. The supernatant was discarded after centrifugation at 2000 rpm for 3 min. Then the resulting cells were washed twice with FACS buffer, added with 100 μL/well of fluorescent secondary antibody (Southern Biotech, 2040-09), with a final concentration of 1 μg/mL, and incubated at 4° C. for 1 h before a centrifugation at 2000 rpm for 3 min. The supernatant was discarded, and the resulting cells were washed twice with FACS buffer, resuspended with 100 μL/well of FACS buffer, and analyzed by a flow cytometer (ACEA Pharma, NovoCyte 2060). The results are shown in FIGS. 3A-5B and Tables 4-9.

Figure 3A:
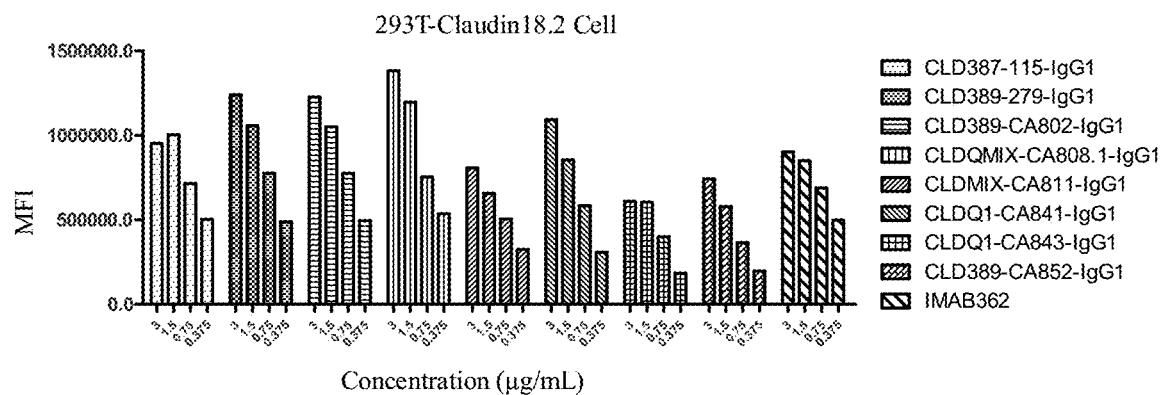
FIGS. 3A-3B show the binding of candidate antibodies to 293T-Claudin18.2 cells measured by flow cytometry.

As shown in FIG. 3A, with 293T-Claudin18.2 cells being the target, the mean fluorescence intensity of candidate antibody CLDQMIX-CA808.1-IgG1 was higher than that of IMAB362 at concentrations of 3 μg/mL, 1.5 μg/mL, 0.75 μg/mL and 0.375 μg/mL. This indicates that the candidate antibody CLDQMIX-CA808.1-IgG1 has a higher affinity to 293T-Claudin18.2 cells at concentrations of 3 μg/mL, 1.5 μg/mL, 0.75 μg/mL and 0.375 μg/mL.

Figure 5A:
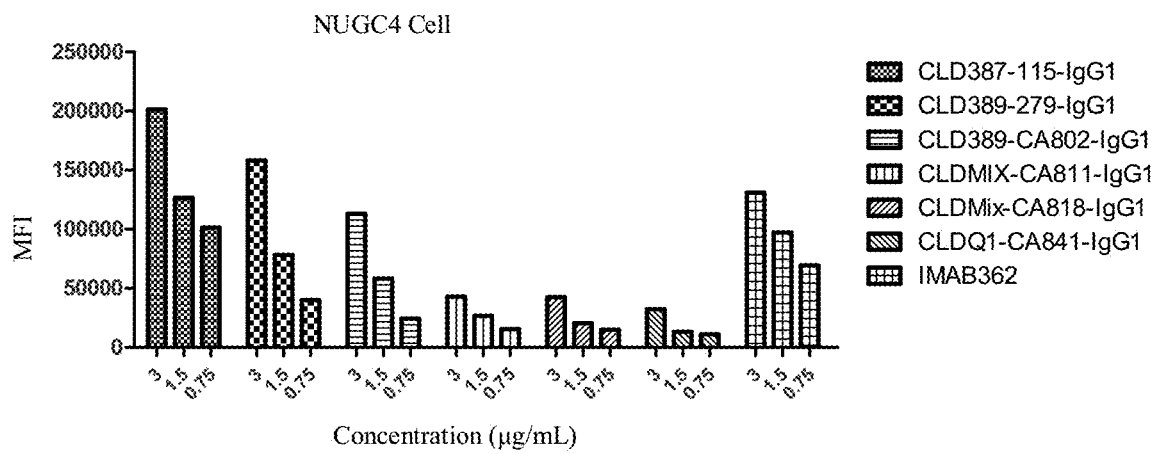
FIGS. 5A-5B show the binding of candidate antibodies to NUGC4 cells measured by flow cytometry.
Figure 5B:
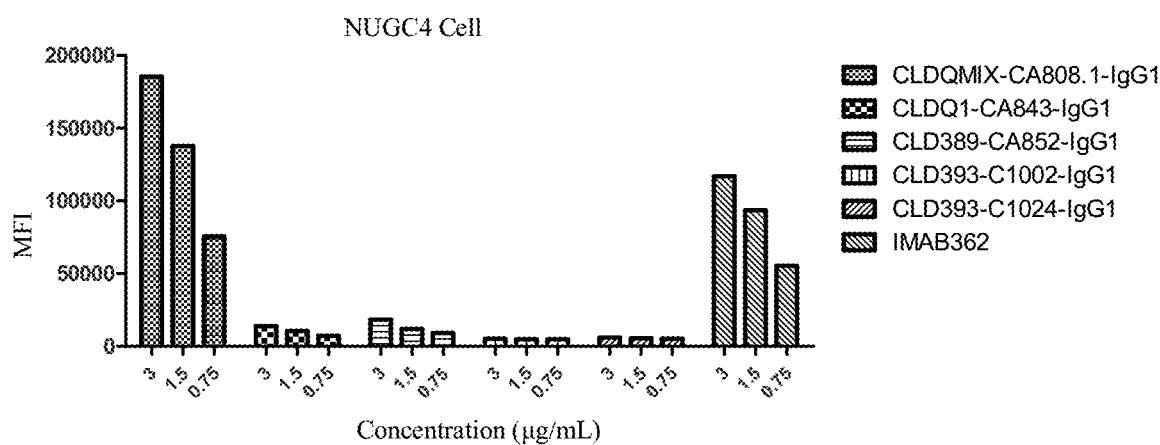

As shown in FIG. 5B, with NUGC4 cells being the target, the mean fluorescence intensity of candidate antibody CLDQMIX-CA808.1-IgG1 was higher than that of IMAB362 at concentrations of 3 μg/mL, 1.5 μg/mL, and 0.75 μg/mL. This indicates that the candidate antibody CLDQMIX-CA808.1-IgG1 has a higher affinity to NUGC4 cells expressing Claudin18.2 at concentrations of 3 μg/mL, 1.5 μg/mL, and 0.75 μg/mL.

As shown in FIG. 3A, with 293T-Claudin18.2 cells being the target, the mean fluorescence intensity of the candidate antibody CLDQ1-CA841-IgG1 was higher than that of IMAB362 at concentrations of 3 μg/mL and 1.5 μg/mL. This indicates that the candidate antibody CLDQ1-CA841-IgG1 has a higher affinity to 293T-Claudin18.2 cells at concentrations of 3 g/mL and 1.5 μg/mL.

Figure 4A:
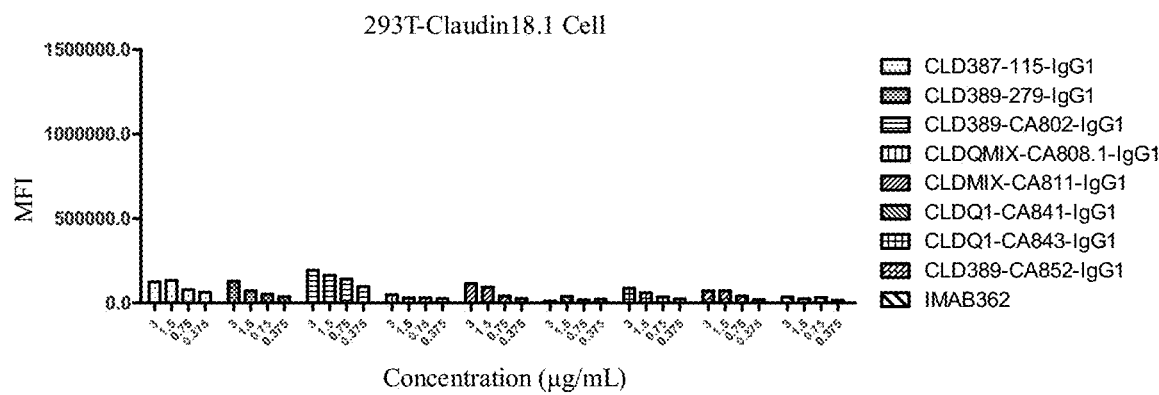
FIGS. 4A-4B show the binding of candidate antibodies to 293T-Claudin18.1 cells measured by flow cytometry.

As shown in FIG. 4A, with 293T-Claudin18.1 cells being the target, the mean fluorescence intensities of the candidate antibodies CLDQMIX-CA808.1-IgG1 and CLDQ1-CA841-IgG1 were similar to that of IMAB362, which were all at lower levels at various concentrations.

The above results show that CLDQMIX-CA808.1-IgG1 and CLDQ1-CA841-IgG1 have better ability of binding cells expressing Claudin18.2, and have weak ability of binding Claudin18.1. It indicates that Claudin18.2 cells are more prone to binding, and specific binding to targets other than Claudin18.2 is less likely to occur in clinical applications, thereby achieving better pharmaceutical effects.

TABLE 4

Binding of candidate antibodies to 293T-Claudin18.2 cells measured by flow cytometry (corresponding to FIG. 3A)

| Antibody ID | Antibody concentration (3 μg/mL) | Antibody concentration (1.5 μg/mL) | Antibody concentration (0.75 μg/mL) | Antibody concentration (0.375 μg/mL) |
|---|---|---|---|---|
| CLD387-115-IgG1 | 952384 | 1002923 | 714249 | 501750 |
| CLD389-279-IgG1 | 1239649 | 1057051 | 775956 | 487518 |
| CLD389-CA802-IgG1 | 1226148 | 1049205 | 773824 | 494669 |
| CLDQMIX-CA808.1-IgG1 | 1382494 | 1196101 | 752733 | 535348 |
| CLDMIX-CA811-IgG1 | 806980 | 657103 | 504375 | 324014 |
| CLDQ1-CA841-IgG1 | 1092233 | 854886 | 583477 | 307641 |
| CLDQ1-CA843-IgG1 | 609424 | 603959 | 399820 | 182880 |
| CLD389-CA852-IgG1 | 741760 | 577688 | 364883 | 196431 |
| IMAB362 | 902134 | 849017 | 688504 | 497940 |

TABLE 5

Figure 3B:
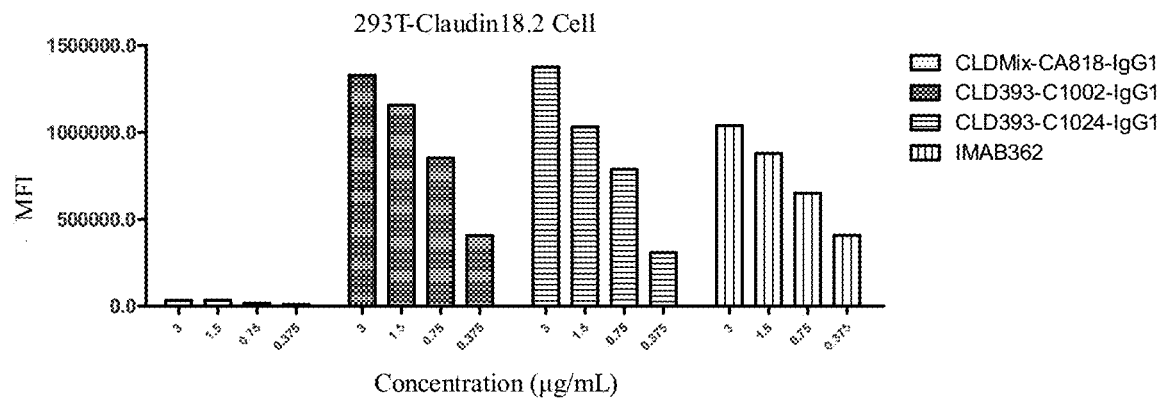

Binding of candidate antibodies to 293T-Claudin18.2 cells measured by flow cytometry (corresponding to FIG. 3B)

| Antibody ID | Antibody concentration (3 μg/mL) | Antibody concentration (1.5 μg/mL) | Antibody concentration (0.75 μg/mL) | Antibody concentration (0.375 μg/mL) |
|---|---|---|---|---|
| CLDMix-CA818-IgG1 | 33274 | 34210 | 17288 | 9356 |
| CLD393-C1002-IgG1 | 1326330 | 1156050 | 852105 | 405515 |
| CLD393-C1024-IgG1 | 1374048 | 1030045 | 787017 | 308011 |
| IMAB362 | 1037843 | 877912 | 649900 | 407382 |

TABLE 6

Binding of candidate antibodies to 293T-Claudin18.1 cells measured by flow cytometry (corresponding to FIG. 4A)

| Antibody ID | Antibody concentration (3 μg/mL) | Antibody concentration (1.5 μg/mL) | Antibody concentration (0.75 μg/mL) | Antibody concentration (0.375 μg/mL) |
|---|---|---|---|---|
| CLD387-115-IgG1 | 124974 | 133585 | 78691 | 63446 |
| CLD389-279-IgG1 | 128702 | 72429 | 52042 | 36901 |

TABLE 6-continued

Binding of candidate antibodies to 293T-Claudin18.1 cells measured by flow cytometry (corresponding to FIG. 4A)

| Antibody ID | Antibody concentration (3 µg/mL) | Antibody concentration (1.5 µg/mL) | Antibody concentration (0.75 µg/mL) | Antibody concentration (0.375 µg/mL) |
|---|---|---|---|---|
| CLD389-CA802-IgG1 | 193720 | 162744 | 140589 | 96678 |
| CLDQMIX-CA808.1-IgG1 | 47521 | 28885 | 29387 | 26004 |
| CLDMIX-CA811-IgG1 | 114724 | 93551 | 40496 | 26022 |
| CLDQ1-CA841-IgG1 | 10958 | 37855 | 18119 | 21489 |
| CLDQ1-CA843-IgG1 | 86333 | 59051 | 35542 | 23218 |
| CLD389-CA852-IgG1 | 70114 | 72110 | 40071 | 18876 |
| IMAB362 | 35584 | 24896 | 31961 | 15638 |

TABLE 7

Figure 4B:
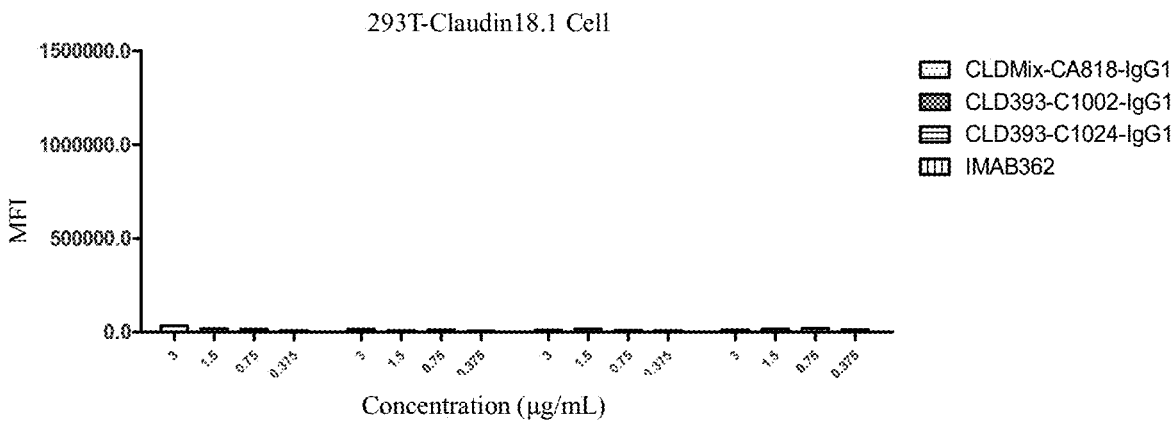

Binding of candidate antibodies to 293T-Claudin18.1 cells measured by flow cytometry (corresponding to FIG. 4B)

| Antibody ID | Antibody concentration (3 µg/mL) | Antibody concentration (1.5 µg/mL) | Antibody concentration (0.75 µg/mL) | Antibody concentration (0.375 µg/mL) |
|---|---|---|---|---|
| CLDMix-CA818-IgG1 | 34418 | 17935 | 15184 | 7957 |
| CLD393-C1002-IgG1 | 15767 | 8615 | 12343 | 6963 |
| CLD393-C1024-IgG1 | 10099 | 17142 | 9851 | 7892 |
| IMAB362 | 12483 | 17319 | 20666 | 12817 |

TABLE 8

Binding of candidate antibodies to NUGC4 cells measured by flow cytometry (corresponding to FIG. 5A)

| Antibody ID | Antibody concentration (3 µg/mL) | Antibody concentration (1.5 µg/mL) | Antibody concentration (0.75 µg/mL) |
|---|---|---|---|
| CLD387-115-IgG1 | 201377 | 126584 | 101395 |
| CLD389-279-IgG1 | 158296 | 78264 | 40032 |
| CLD389-CA802-IgG1 | 113085 | 58148 | 24412 |
| CLDMIX-CA811-IgG1 | 43084 | 26853 | 15543 |
| CLDMix-CA818-IgG1 | 42617 | 20432 | 15029 |
| CLDQ1-CA841-IgG1 | 32421 | 13208 | 11119 |
| IMAB362 | 130923 | 97087 | 69564 |

TABLE 9

Binding of candidate antibodies to NUGC4 cells measured by flow cytometry (corresponding to FIG. 5B)

| Antibody ID | Antibody concentration (3 µg/mL) | Antibody concentration (1.5 µg/mL) | Antibody concentration (0.75 µg/mL) |
|---|---|---|---|
| CLDQMIX-CA808.1-IgG1 | 185377 | 137723 | 75649 |
| CLDQ1-CA843-IgG1 | 13935 | 10612 | 7234 |
| CLD389-CA852-IgG1 | 18351 | 11955 | 9229 |
| CLD393-C1002-IgG1 | 5170 | 4891 | 4946 |
| CLD393-C1024-IgG1 | 6141 | 5643 | 5210 |
| IMAB362 | 116862 | 93509 | 55403 |

6 3.3 ADCC of Antibodies

Sterile fetal bovine serum was thawed and added to an RPMI1640 medium at a ratio of 1:99 to give an ADCC buffer. PBMC cells were thawed and incubated overnight in an incubator at 37° C./5% $CO_2$. The density of target cells (293T-Claudin18.1 or 18.2) was adjusted with the ADCC Buffer to $2\times10^5$ cells/mL, and 50 µL of the target cells was added to each well of a 96-well round-bottom plate. The antibodies to be tested were diluted by 10× with the ADCC Buffer from 10 µg/mL or 50 µg/mL, then 50 µL of the diluted antibody was added to each well of the 96-well round-bottom plate coated with the target cells, and incubated in an incubator at 37° C./5% $CO_2$ for 30-60 min. PBMC cells were collected and diluted with the ADCC buffer to a density from $2\times10^6$ cells/mL to $5\times10^6$ cells/mL, then 100 µL of the diluted cells was added to each well of the 96-well round-bottom plate coated with the target cells and the sample to be tested, and incubated in an incubator at 37° C./5% $CO_2$ for 4-6 h. After incubation, the cells were centrifuged at 300 g for 2-5 min, then 50 µL of supernatant was carefully pipetted to a new 96-well flat-bottom plate, and 50 µL of LDH test solution (Promega, G1780) was added. The cells were then incubated in an incubator at 37° C./5% $CO_2$ for 30 min. A terminating buffer was added after incubation. The OD value at 490 nm was measured by a microplate reader, with a background wavelength being 650 nm. The results are shown in FIGS. 6A-6B and Tables 10-11.

Figure 6A:
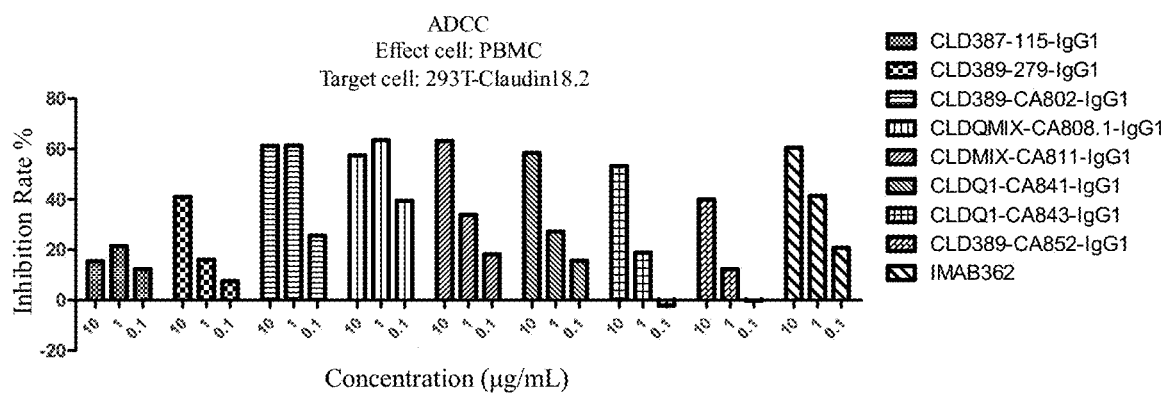
FIGS. 6A-6B show the ADCC of candidate antibodies on 293T-Claudin18.2 cells.
Figure 6B:
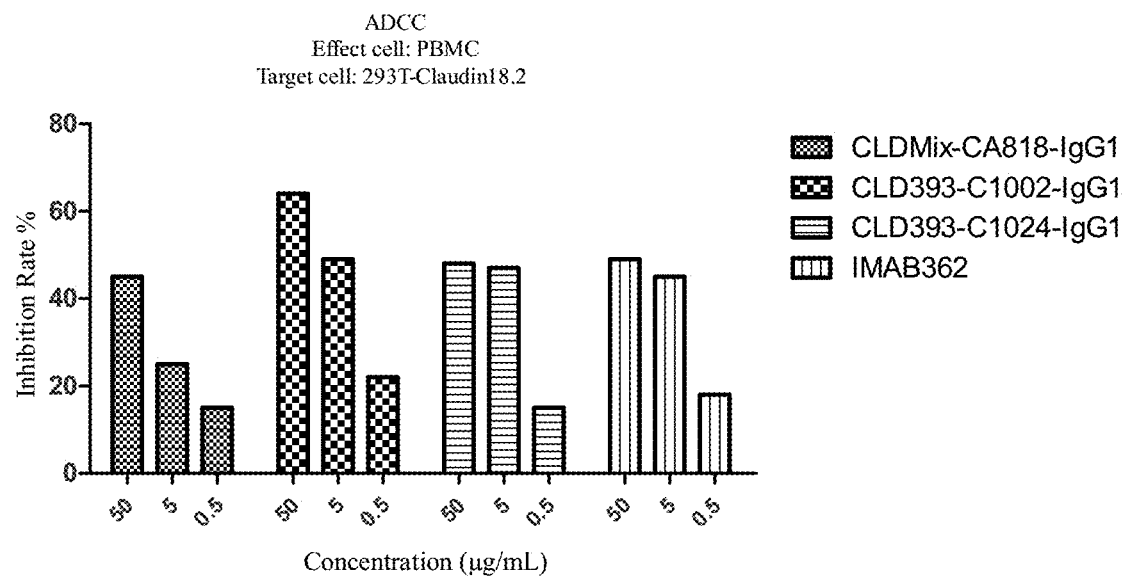

As shown in FIG. 6A, with 293T-Claudin18.2 as target and PBMC as effector cell, the inhibition rate of the candidate antibody CLDQMIX-CA808.1-IgG1 to the target cells at concentrations of 1 µg/mL and 0.1 µg/mL was higher than that of the reference antibody IMAB362 at the corresponding concentrations, suggesting that the candidate antibody CLDQMIX-CA808.1-IgG1 has a better ability of mediating ADCC than the reference antibody IMAB362 at the concentrations of 1 µg/mL and 0.1 µg/mL. This indicates that CLDQMIX-CA808.1-IgG1 can kill target cells expressing Claudin18.2 better and has better pharmaceutical effects.

TABLE 10

ADCC of candidate antibodies on 293T-Claudin18.2 cells (corresponding to FIG. 6A)

| | Inhibition rate, % | | |
|---|---|---|---|
| Antibody ID | Antibody concentration (10 µg/mL) | Antibody concentration (1 µg/mL) | Antibody concentration (0.1 µg/mL) |
| CLD387-115-IgG1 | 15.48077 | 21.48077 | 12.28077 |
| CLD389-279-IgG1 | 40.95 | 16.05 | 7.530769 |
| CLD389-CA802-IgG1 | 61.21154 | 61.38846 | 25.60769 |
| CLDQMIX-CA808.1-IgG1 | 57.43462 | 63.55769 | 39.42692 |
| CLDMIX-CA811-IgG1 | 63.24208 | 33.91539 | 18.17308 |
| CLDQ1-CA841-IgG1 | 58.48615 | 27.23462 | 15.64231 |
| CLDQ1-CA843-IgG1 | 53.19346 | 18.85385 | −2.088462 |
| CLD389-CA852-IgG1 | 39.92692 | 12.28077 | −0.2115385 |
| IMAB362 | 60.56292 | 41.36427 | 20.82923 |

TABLE 11

ADCC of candidate antibodies on 293T-Claudin18.2 cells (corresponding to FIG. 6B)

| | Inhibition rate, % | | |
|---|---|---|---|
| Antibody ID | Antibody concentration (50 µg/mL) | Antibody concentration (5 µg/mL) | Antibody concentration (0.5 µg/mL) |
| CLDMix-CA818-IgG1 | 45 | 25 | 15 |
| CLD393-C1002-IgG1 | 64 | 49 | 22 |
| CLD393-C1024-IgG1 | 48 | 47 | 15 |
| IMAB362 | 49 | 45 | 18 |

Cells were counted and diluted with an ADCC buffer to 4×10⁵ cells/mL. A proper amount of the sample was taken for a serial dilution. Effector cells Jurkat (G7011, Promega) were centrifuged at 1500 rpm with the supernatant discarded, and resuspended with 1% FBS RPMI-1640 medium. The cells were counted and diluted with the ADCC buffer to 8×10⁵ cells/mL. Then 25 µL of the target cells was added to each well of a white 96-well plate (3917, Costar), and 25 µL of the serially diluted antibodies was added to each well coated with the target cells. 25 µL of effector cells (Jurkat) was added to each well in a ratio of effector cells to target cells of 20000:10000. Then the 96-well plate was incubated in a cell incubator for 5 h, and equilibrated at room temperature. Then 75 µL of a Bio-Glo color-developing buffer (G7940, Promega) was added to each well for a 15-min reaction, and the plate was detected on a Tecan microplate reader (chemiluminescence). The results are shown in FIGS. 7A-8 and Tables 12-13.

Figure 7A:
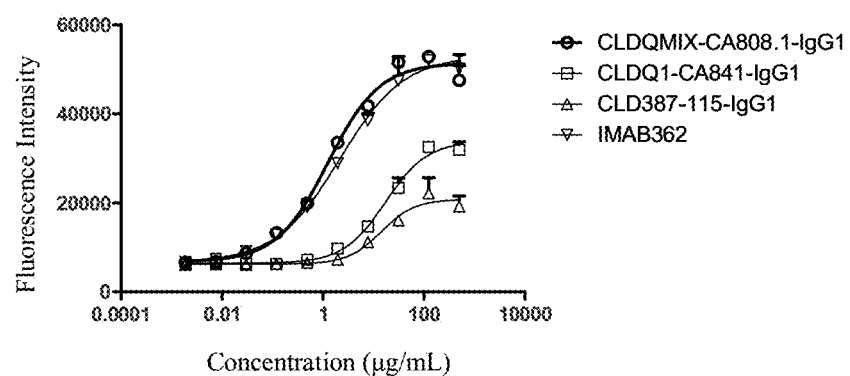
FIGS. 7A-7B show the ADCC of candidate antibodies on NUGC4 cells.
Figure 8:
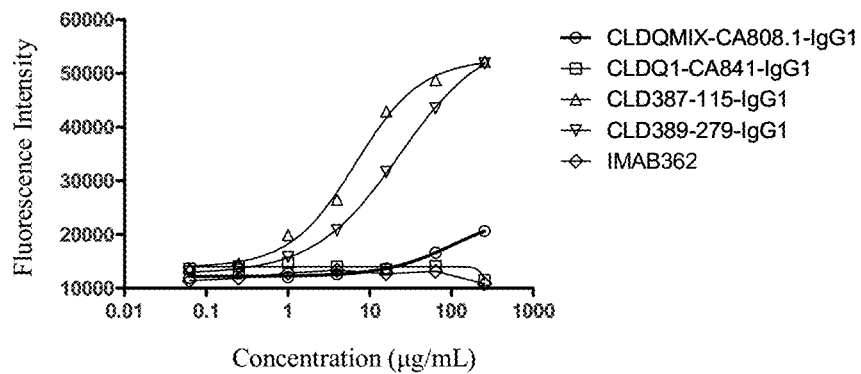
FIG. 8 shows the ADCC of candidate antibodies on 293T-Claudin18.1 cells.

As shown in FIG. 7A, with NUGC4 being the target, the $EC_{50}$ value of CLDQMIX-CA808.1-IgG1 was 1.264 µg/mL, which was less than that of the reference antibody IMAB362 of 2.154 µg/mL, indicating that the candidate antibody CLDQMIX-CA808.1-IgG1 has a better ability of mediating ADCC than the reference antibody IMAB362. This indicates that CLDQMIX-CA808.1-IgG1 can kill target cells expressing Claudin18.2 better and has better pharmaceutical effects.

TABLE 12

ADCC of candidate antibodies on NUGC4 cells (corresponding to FIG. 7A)

| Antibody ID | $EC_{50}$ (µg/mL) | Antibody ID | $EC_{50}$ (µg/mL) |
|---|---|---|---|
| CLDQMIX-CA808.1-IgG1 | 1.264 | CLD387-115-IgG1 | 14.27 |
| CLDQ1-CA841-IgG1 | 17.33 | IMAB362 | 2.154 |

TABLE 13

Figure 7B:
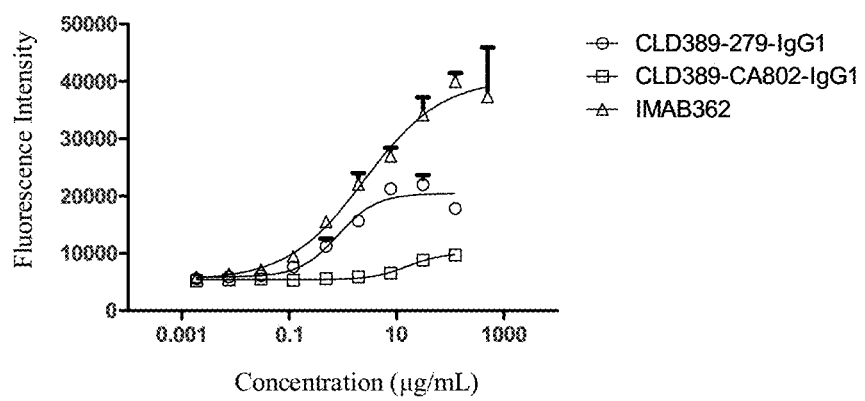

ADCC of candidate antibodies on NUGC4 cells (corresponding to FIG. 7B)

| Antibody ID | $EC_{50}$ (µg/mL) | Antibody ID | $EC_{50}$ (µg/mL) |
|---|---|---|---|
| CLD389-279-IgG1 | 0.81 | IMAB362 | 2.56 |
| CLD389-CA802-IgG1 | 15.73 | / | / |

7 Example 4. Modification of Fc Terminus of Anti-Claudin 18.2 Antibodies 8 4.1 Modification of Fc Terminus of Antibodies In order to enhance the ADCC of antibodies and change the affinity between the antibodies and Fc receptor, the Fc terminus of the antibody was mutated. The mutated amino acid sequence of heavy chain constant region is set forth in SEQ ID NO: 18. The resulting antibody was named CLDQ-Mix-CA808.1-IgG1-VLPLL.

9 4.2 Affinity of Modified Antibody to Fc Receptors 4.2.1 Affinity of Antibody to Human FcRn The antibody binding kinetics was determined by Octet$^{RED}$ 96 system based on the biolayer interferometry (BLI). Human FcRn (ACROBiosystems, FCM-H82W4, 1 µg/mL) was loaded to Streptavidin (SA) Dip and Read™ Biosensors with a loading height of 0.2 nm. The antibody was serially diluted by 2× with PBST from 33.3 mM, and a blank control was set. The Association time was set to 150 s, and the dissociation time was set to 100 s. After the assay, the equilibrium dissociation constant ($k_D$) was calculated using Steady State Analysis.

4.2.2 Affinity of Antibody to Human CD32a(H)

The antibody binding kinetics was determined by Octet$^{RED}$ 96 system based on the biolayer interferometry (BLI). Human CD32a(H) (Sino Biological, 10374-H27H1-B, 1 µg/mL) was loaded to Streptavidin (SA) Dip and Read™ Biosensors with a loading height of 0.2 nm. The antibody was serially diluted by 2× with PBST from 1000 mM, and a blank control was set. The Association time was set to 150 s, and the dissociation time was set to 100 s. After the assay, the equilibrium dissociation constant ($k_D$) was calculated using Steady State Analysis.

4.2.3 Affinity of Antibody to Human CD16a(V)

The antibody binding kinetics was determined by Octet$^{RED}$ 96 system based on the biolayer interferometry (BLI). Human CD16a(V) (Sino Biological, 10389-H27H1-B, 0.5 µg/mL) was loaded to Streptavidin (SA) Dip and Read™ Biosensors with a loading height of 0.5 nm. The antibody was serially diluted by 2× with PBST from 166.7 mM, and a blank control was set. The Association time was set to 30 s, and the dissociation time was set to 100 s. After the assay, association constant ($k_{on}$), dissociation constant ($k_{dis}$) were calculated by curve fitting with a 1:1 model and equilibrium dissociation constant ($k_D$) were calculated in the ratio of $k_d/k_a$.

4.2.4 Affinity of Antibody to Human CD16a(F)

The antibody binding kinetics was determined by Octet$^{RED}$ 96 system based on the biolayer interferometry (BLI). Human CD16a(F) (Sino Biological, 10389-H27H-B, 0.5 μg/mL) was loaded to Streptavidin (SA) Dip and Read™ Biosensors with a loading height of 0.5 nm. The antibody was serially diluted by 2× with PBST from 333.3 mM, and a blank control was set. The Association time was set to 30 s, and the dissociation time was set to 100 s. After the assay, association constant ($k_{on}$), dissociation constant ($k_{dis}$) were calculated by curve fitting with a 1:1 model and equilibrium dissociation constant ($k_D$) were calculated in the ratio of $k_d/k_a$.

4.2.5 Affinity of Antibody to Human CD32b

The antibody binding kinetics was determined by Octet$^{RED}$ 96 system based on the biolayer interferometry (BLI). Human CD32a(H) (Sino Biological, 10374-H27H1-B, 1 μg/mL) was loaded to Streptavidin (SA) Dip and Read™ Biosensors with a loading height of 0.2 nm. The antibody was serially diluted by 2× with PBST from 2000 mM, and a blank control was set. The Association time was set to 40 s, and the dissociation time was set to 50 s. After the assay, the equilibrium dissociation constant ($k_D$) was calculated using Steady State Analysis.

As shown in Table 14, the affinity of CLDQMIX-CA808.1-IgG1-VLPLL to agonistic receptors, particularly Human CD16a(F), was greatly improved, thus better promoting the ADCC in subjects.

TABLE 14

Affinity of candidate antibody to Fc receptors

| | FC receptor | KD (M) of CLDQMIX-CA808.1-IgG1 | KD (M) of CLDQMIX-CA808.1-IgG1 VLPLL | Ratio of KD |
|---|---|---|---|---|
| Agonistic receptors | Human CD32a(H) | 4.10E-07 | 3.00E-07 | 1.37↑ |
| | Human CD16a(V) | 1.07E-07 | 5.41E-08 | 1.98↑ |
| | Human CD16a(F) | 5.66E-07 | 1.19E-07 | 4.75↑ |
| | Human FcRn | 6.93E-09 | 5.27E-09 | 1.31↑ |
| Inhibitory receptor | Human CD32b | 3.20E-06 | 3.00E-06 | — |

10 Example 5. Pharmacodynamics of Anti-Claudin18.2 Antibodies

Human gastric cancer NUGC4 cells (JCRB Cell Bank, catalog number: JCRB0834) were cultivated in an RPMI1640 medium containing 10% fetal bovine serum, 100 U/mL penicillin and 100 μg/mL streptomycin through monolayer culture in vitro in an incubator at 37° C./5% $CO_2$. The cells were digested with trypsin-EDTA twice a week for passaging as per conventional practice. At a cell saturation of 80%-90% and a required number, the cells were harvested, counted and grafted into BALB/c nude mice (female, 6-8 weeks old, 18-22 g) (Shanghai Lingchang Biotechnology Co., Ltd.). 0.2 mL (1×10$^6$ cells) of NUGC4 cells (along with matrigel in a volume ratio of 1:1) was subcutaneously grafted on the right back of each mouse, and the mice were randomized when the mean tumor volume was approximately 60-70 mm$^3$. The animals were weighed before administration and the tumor volume was measured. The mice were randomized by the tumor volume (randomized block design), 8 in each group. The weight was measured twice a week, and the tumor diameter was measured with a vernier caliper twice a week. The tumor volume was calculated using the following formula: V=0.5×a×b$^2$, where, a and b represent the long diameter and short diameter of the tumor respectively. The results are shown in FIG. 9 and Table 15.

Figure 9:
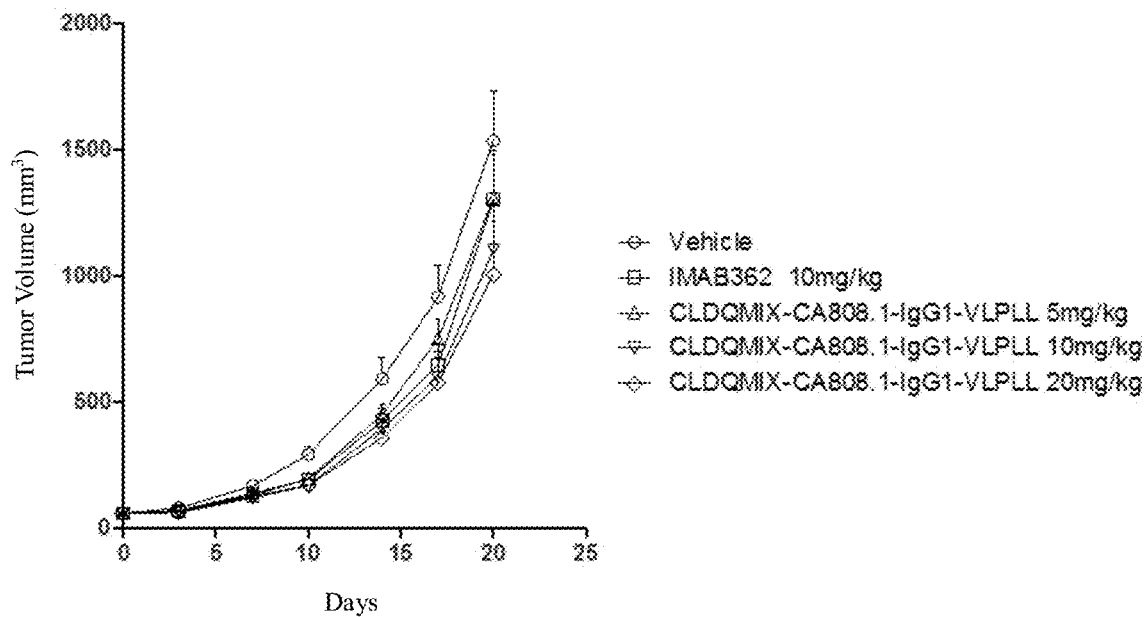
FIG. 9 shows the pharmacodynamics of candidate antibodies.

As shown in FIG. 9, the tumor inhibitory effect of 5 mg/kg CLDQMIX-CA808.1-IgG1-VLPLL was comparable to that of 10 mg/kg IMAB362. Compared with 10 mg/kg IMAB362, 10 mg/kg CLDQMIX-CA808.1-IgG1-VLPLL demonstrated better tumor inhibitory effect. This indicated that the CLDQMIX-CA808.1-IgG1-VLPLL antibody has better tumor inhibitory activity than IMAB362, and the inhibitory effect of CLDQMIX-CA808.1-IgG1-VLPLL on tumors is dose-dependent. The tumor inhibitory effect increases with the dose.

TABLE 15

Pharmacodynamics of candidate antibodies (corresponding to FIG. 9)

| Antibody ID | Final tumor volume (mm$^3$) |
|---|---|
| Vehicle | 1536.5 ± 195.8 |
| IMAB362 10 mg/kg | 1301.0 ± 177.2 |
| CLDQMIX-CA808.1-IgG1-VLPLL 5 mg/kg | 1307.8 ± 186.4 |
| CLDQMIX-CA808.1-IgG1-VLPLL 10 mg/kg | 1103.3 ± 186.5 |
| CLDQMIX-CA808.1-IgG1-VLPLL 20 mg/kg | 1006.4 ± 207.1 |

11 Example 6. Preparation of Claudin18.2-Specific Chimeric Antigen Receptor-Modified T Cells

12 6.1 Preparation of Gene Fragment of Chimeric Antigen Receptor

In the present invention, a fusion gene fragment was designed in the following order of coding genes: CD8a signal peptide, CA841 scFv VH-linker-CA841 scFv VL, CD8 hinge region, CD8 transmembrane region, and 4-1BB and CD3ζ intracellular signaling regions, and the fusion gene was directly synthesized by gene synthesis techniques, allowing the expressed chimeric antigen receptor to have an amino acid sequence of scFv VH-linker-scFv VL-CD8 hinge-CD8TM-4-1BB-CD3ζ. The linker had a sequence of GGGGSGGGGSGGGGS (SEQ ID NO: 46), the CD8α signal peptide had a sequence of SEQ ID NO: 21, the CD8 hinge region (CD8 hinge) had a sequence of SEQ ID NO: 22, the CD8 transmembrane region (CD8 TM) had a sequence of SEQ ID NO: 23, the 4-1BB had a sequence of SEQ ID NO: 24, and the CD3ζ had a sequence of SEQ ID NO: 25.

Figure 10:
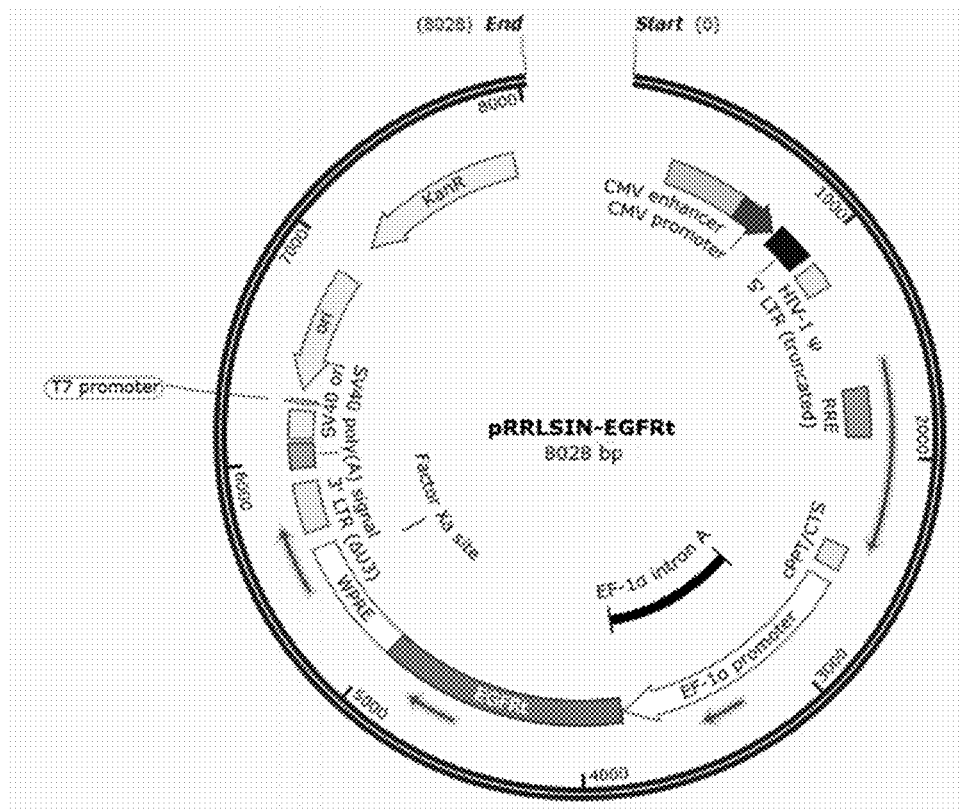
FIG. 10 shows a structural schematic of plasmid pRRLSIN-EGFRt.

The whole gene of pRRLSIN lentivirus vector containing a human EF1a promoter was synthesized, and the green fluorescent protein (GFP) sequence was replaced by an EGFRt marker protein sequence to give a pRRLSIN-EGFRt vector (see FIG. 10).

13 6.2 Construction of Lentiviral Expression Vector of Chimeric Antigen Receptor In the example, the vector system used to construct the lentivirus plasmid vector of the present invention was a third generation self-inactivated lentivirus vector system. The system has three plasmids: a pMDLg-pRRE packaging plasmid (Unibio, VT1449) encoding protein Gag/Pol, a pRSV-rev packaging plasmid (Unibio, VT1445) encoding Rev protein, and an envelope plasmid PMD2.G (Unibio, VT1443) encoding VSV-G protein.

Figure 11:
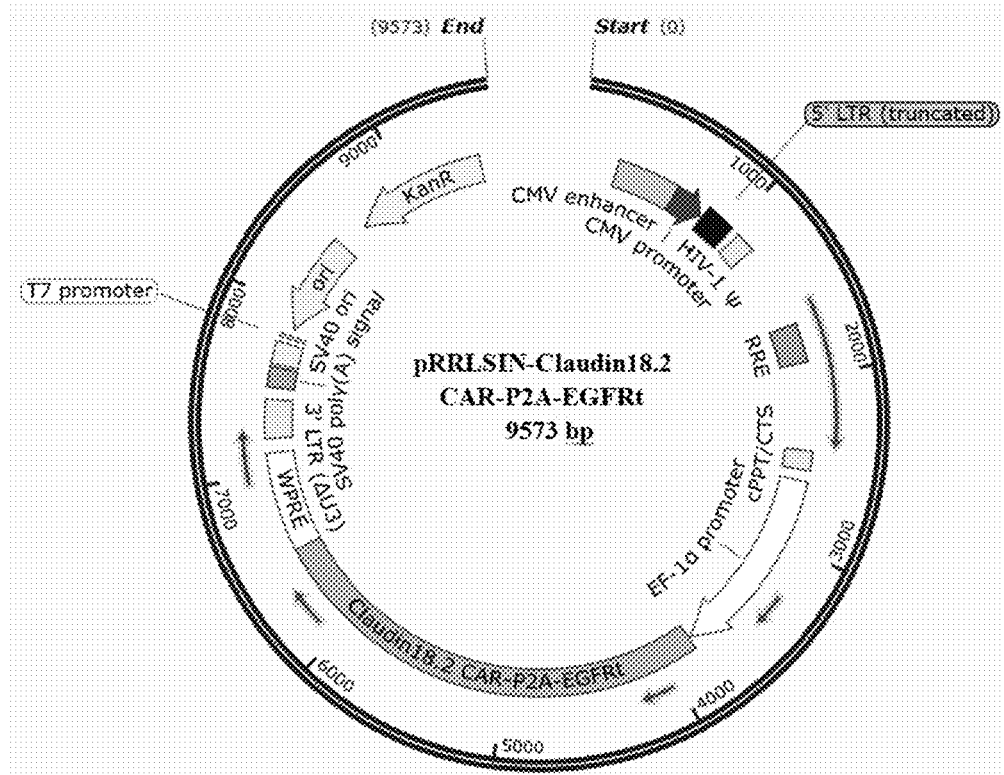
FIG. 11 shows a structural schematic of recombinant plasmid pRRLSIN-Claudin18.2CAR-P2A-EGFRt.

In the example, a lentivirus expression vector expressing specific CAR and EGFRt (SEQ ID NO: 27) linked by P2A (SEQ ID NO: 26) was constructed, and the target gene obtained in Section 6.1 was linked to the pRRLSIN-EGFRt vector to form a recombinant plasmid named pRRLSIN-Claudin18.2CAR-P2A-EGFRt (see FIG. 11). The specific sequence was pRRLSIN-CD8α-scFv VH-linker-scFv VL-CD8hinge-CD8TM-4-1BB-CD3ζ-P2A-EGFRt. After verified by enzyme digestion and sequencing, the successfully constructed vector was ready to package. CAR-P2A-EGFRt was transcribed into a single mRNA, but finally translated into two peptide chains of EGFRt and anti-Claudin18.2 chimeric antigen receptor. Anti-Claudin18.2 CAR was located on the cell membrane under the direction of the CD8a signal peptide.

The four sequences containing the target CAR obtained in the example are as follows: scFv CA808.1-CD8hinge-CD8TM-4-1BB-CD3ζ-P2A-EGFRt (hereinafter referred to as CN01) scFv CA841-CD8hinge-CD8TM-4-1BB-CD3ζ-P2A-EGFRt (hereinafter referred to as CN02) scFv C279-CD8hinge-CD8TM-4-1BB-CD3ζ-P2A-EGFRt (hereinafter referred to as CN03) scFv C115-CD8hinge-CD8TM-4-1BB-CD3ζ-P2A-EGFRt (hereinafter referred to as CN04)

6.3 Preparation of Chimeric Antigen Receptor Lentivirus

The pRRLSIN-Claudin18.2CAR-P2A-EGFRt expression plasmid and pMDLg-pRRE, pRSV-rev and pMD2.G helper plasmids were extracted and mixed with the transfection reagent polyethyleneimine (PEI) in a certain ratio to co-transfect 293T cells. The major procedures are as follows:

(1) The 293T cells passaged to 5-8th generations (ATCC CRL-3216) were seeded at a cell density of $7 \times 10^6$ in a DMEM medium (purchased from GIBCO) containing 10% FBS (purchased from GIBCO) in 75 cm³ cell culture flasks. After mixing, the cells were cultivated in a $CO_2$ incubator at 37° C./5% $CO_2$ for 24 h before transfection. A cell aggregation of about 70-80% was observed on the next day, and the cells were transfected.

(2) 24 h later, the target expression plasmid and the pMDLg-pRRE, pRSV-rev and pMD2.G helper plasmids were mixed in a weight ratio of 4:3:2:2, and diluted with an Opti-MEM medium (purchased from GIBCO) to give a solution A. A PEI diluent was prepared in a ratio of total plasmids:PEI=3:1, and diluted with the Opti-MEM medium to obtain a solution B. The solutions A and B were mixed well and incubated at room temperature for 15 min.

(3) The 293T cells were immobilized on a plate, and slowly added with the plasmid-PEI mixture. The resulting mixture was shaken gently, and cultivated in a $CO_2$ incubator at 37° C./5% $CO_2$ for 4-6 h. After incubation, the medium was replaced with a fresh DMEM medium containing 10% FBS.

(4) After 48 h and 96 h of transfection, the culture supernatant containing viruses was collected and centrifuged at 3000 rpm at 4° C. for 5 min. The supernatant was filtered through a 0.45 μm filter, mixed with PEG8000/NaCl in a volume ratio of 4:1, incubated at 4° C. for 2-3 h, and centrifuged at a high speed for 30 min. The supernatant was discarded and the precipitate was resuspended with pre-cooled T cell medium X-VIVO 15 (Lonza, 04-418Q) or PBS to give a virus concentrate which was stored at −80° C. for later use.

6.4 Lentivirus Titer Assay

Figure 12:
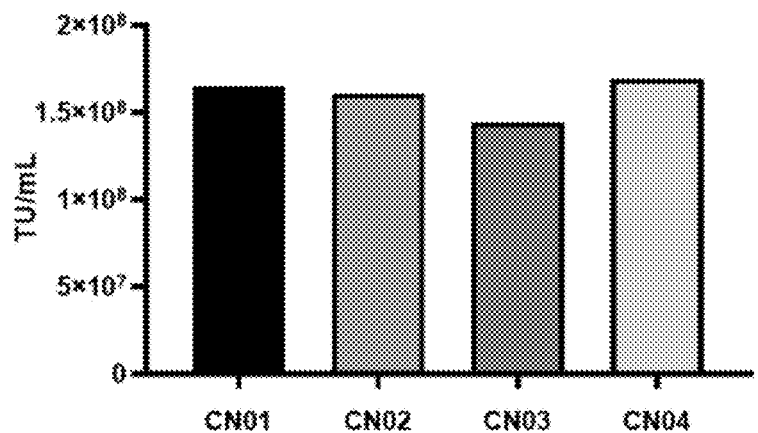
FIG. 12 shows the lentivirus activity titers of different chimeric antigen receptors.

In the example, the biological activity titer of lentivirus was determined by infecting cells. The 293T cells were used for lentivirus activity assay, and $1 \times 10^5$ cells were inoculated to each well of a 24-well culture plate. 1 mL of fresh DMEM medium containing 10% FBS was added to each well. The mixture was diluted to a final concentration of 6 μg/mL with transfection additive Polybrene. The lentivirus concentrate was serially diluted by 3× to the 5th concentration, added at 1 μL/well in duplicate, and mixed well. The cells were incubated in a $CO_2$ incubator at 37° C./5% $CO_2$ for 24 h. After 24 h, the cells were digested, and the positive rate of protein expression of CAR or EGFRt was detected by a flow cytometer using an anti-human IgG(Fab)$_2$ (Jackson ImmunoResearch, 109-065-006) or anti-human EGFRt (Biolegend, 352904) flow dye. The titer was calculated by the following formula: lentivirus activity titer (TU/mL)=positive rate×dilution factor×100×10$^5$. The activity titers of lentivirus concentrates of the above CAR (CN01, CN02, CN03 and CN04) packaged by PEI transfection were greater than $1 \times 10^8$ TU/mL (FIG. 12).

6.5 Preparation of T Lymphocytes

Peripheral blood mononuclear cells (PBMCs) purchased from AllCells were marked with microbeads through a CD3 MicroBeads human-lyophilized Kit (purchased from Miltenyi Biotech). CD3+ T lymphocytes with high purity were selected, with a proportion of CD3 positive T cells over 95%. The purified T cells were activated and proliferated using a human CD3CD28 T cell activator (Dynabeads Human T-Activator CD3/CD28, Thermo Fisher, 11132D).

6.6 Lentivirus-Transduced T Lymphocytes

Figure 13:
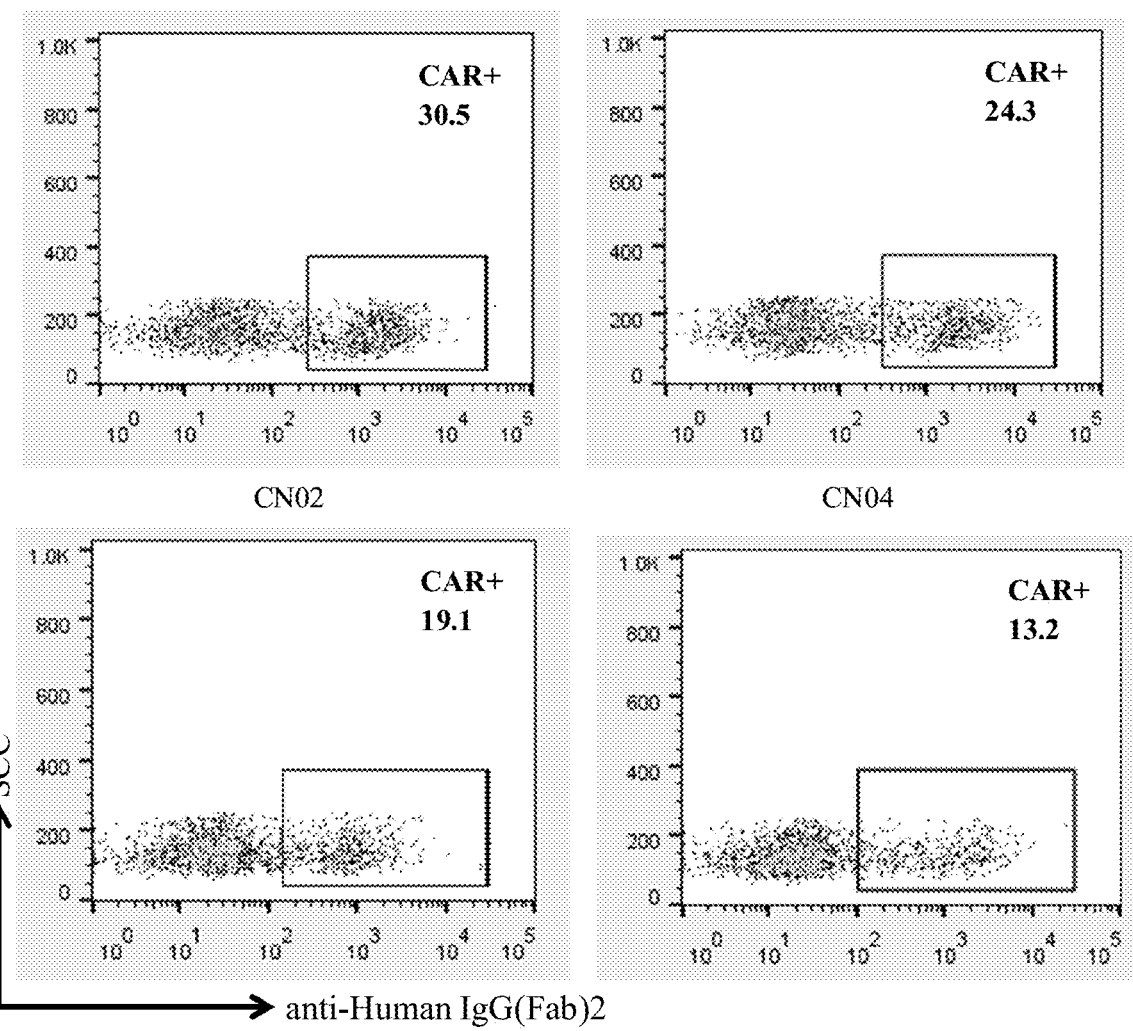
FIG. 13 shows the positive rates of T lymphocytes expressing different chimeric antigen receptors.

CAR-T cells were obtained by transducing T cells with the lentivirus prepared in Section 6.3. After stimulated and activated for 24-48 h, T lymphocytes from Section 6.5 were observed using microscopy for their activation. Activated T lymphocytes are larger in volume with elongated or irregular shape. The activated T lymphocytes were collected, centrifuged and resuspended in a T cell medium X-VIVO 15 (Lonza, 04-418Q) with a final concentration of 10 ng/ml IL-7 and 5 ng/ml IL-15 and a final volume of 1 mL, and added to a 12-well culture plate. The lentivirus was diluted to MOI=3-5 with the same medium and mixed with $1 \times 10^6$ activated T lymphocytes for infection. The mixture was incubated overnight on a 24-well plate in an incubator at 37° C./5% $CO_2$. The next day, the cells were centrifuged again and the medium was refreshed. The cell density was measured every 2 days thereafter, and the cells were further expanded with the cell density controlled at NMT $2 \times 10^6$ cells/mL. After the T cells were co-incubated with the lentivirus for 48-72 h, the expression of different chimeric antigen receptors was determined by flow cytometry. With non-transduced T lymphocytes as negative control, the positive rates of T lymphocytes expressing different chimeric antigen receptors are shown in Table 16 (FIG. 13).

TABLE 16

Positive rates of T lymphocytes expressing different chimeric antigen receptors

| Cells transfected with the following CAR | Positive rate of CAR |
| --- | --- |
| CN01 | 30.5% |
| CN02 | 19.1% |
| CN03 | 24.3% |
| CN04 | 13.2% |

After being infected with lentiviruses packaging different chimeric antigen receptors, T lymphocytes were cultivated for about 9 days, reaching about 300× expansion, which indicated that T lymphocytes expressing different chimeric antigen receptors could be expanded in vitro to a certain extent, providing a guarantee for subsequent in vitro functional studies and pharmacodynamic studies in animals.

6.7 In Vitro Toxicity Assay
14 6.7.1 Target Specificity Assay

Figure 14:
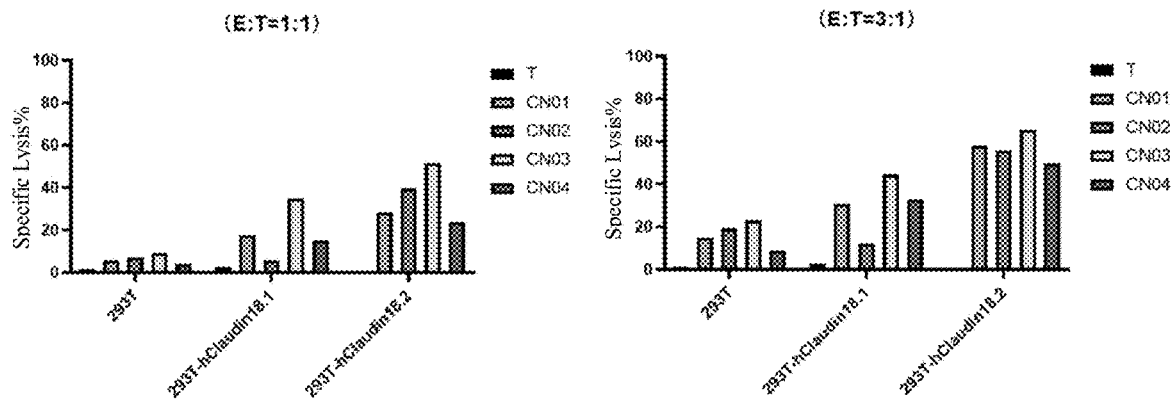
FIG. 14 shows the specific lysis assay of Claudin18.2 CAR-T cells with different scFvs in vitro.
Figure 15:
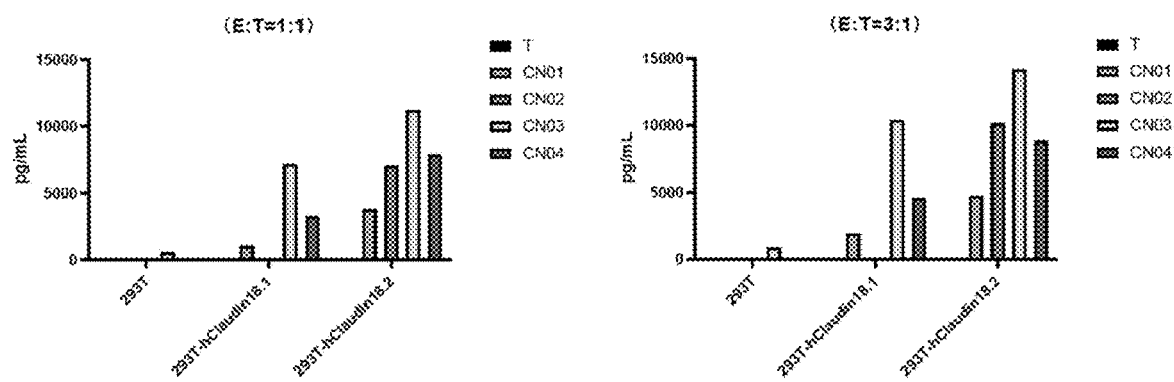
FIG. 15 shows the release of IFN-gamma cytokines in supernatant of co-incubated Claudin18.2 CAR-T cells with different scFvs and different 293T cells.

Claudin-18 has two splicing variants, i.e., Claudin 18.1 and Claudin 18.2, with only eight amino acid alterations in sequence. Claudin 18.1 is selectively expressed in normal lung cells, while Claudin 18.2 is highly restricted in normal cells, but is frequently ectopically activated and overexpressed in multiple tumors (e.g., gastric cancer, lung cancer, pancreatic cancer). In the example, with 293T cells (purchased from KYinno, KC-0990/KC-0986) overexpressing Claudin18.1 protein and Claudin18.2 protein being the target cells and prepared Claudin18.2 CAR-T with different scFvs being the effector cell, a co-incubation system of CAR-T cells and target cells was established using 293T cells, 293T cells overexpressing Claudin18.2 protein and 293T cells overexpressing Claudin18.1 protein in different E:T (effector cells:target cells) ratios. The specific response of CAR-T to the two proteins was evaluated by measuring the lysis rate of tumor cells. The results of in vitro assay (FIG. 14) demonstrated that, with a fixed number of tumor cells, the efficiency of killing tumor cells ranged from 20%-50% at 24 h (Table 17) when the prepared Claudin18.2 CAR-T with different scFvs (CN01, CN02, CN03, CN04) was co-incubated with 293T-hClaudin18.2 cells at E:T ratios of 1:1 and 3:1. When co-incubated with 293T-hClaudin18.1 cells at E:T ratios of 1:1 and 3:1, the prepared Claudin18.2 CAR-T cells with different scFvs were significantly different in specific lysis ability against 293T-hClaudin18.1 cells, among which the CN02 CAR-T had no significant specific lysis ability against 293T-hClaudin18.1 cells, while the CN01, CN03 and CN04 CAR-T had different degrees of specific lysis ability against 293T-hClaudin18.1 cells. The specific response of CAR-T cells was also evaluated by measuring the content of cytokines (INF-gamma) secreted into the culture supernatant. The difference in release of IFN-gamma cytokines in supernatant of the Claudin18.2 CAR-T (CN01, CN02, CN03, CN04) with different scFvs and the 293T-hClaudin18.1 cells was consistent with the results of killing assay (FIG. 15 and Table 18). The IFN-gamma cytokines in 293T-hClaudin18.1 cells co-incubation supernatant in CN02 group was significantly lower than that in CN01, CN03 and CN04 groups.

Specific lysis assay: an LDH Release Assay Kit (Dojindo, CK12) was used for assay, which is an INT chromogenic reaction catalyzed by diaphorase, and measures the activity of LDH released during cytotoxicity via colorimetry. Damage to the cell membrane structure caused by cell apoptosis or necrosis will lead to release of enzymes in cytoplasm into the cultures, including lactate dehydrogenase (LDH) with relatively stable enzymatic activity. The cytotoxicity can be quantitatively analyzed by activity assay of LDH released from lysed cells into the cultures. LDH release is considered as an important indicator of cell membrane integrity and is widely used for cytotoxicity assay.

Cytokine assay: Human IFN-gamma ELISA kit (R&D Systems, SIF50) was used for measuring cytokines, which is based on the immobilization of an antigen or antibody and enzymatic labeling of the antigen or antibody. The antigen or antibody that binds to the surface of a solid carrier retains the immunological activity, while the enzyme labeled antigen or antibody retains both immunological activity and enzymatic activity. During the assay, the test substance (the antigen or antibody) in the sample are bound to the immobilized antibody or antigen. Non-binding substances are removed by washing, and the enzyme-labeled antigen or antibody is added. In this case, the amount of enzyme immobilized is associated with the amount of the test substance in the sample. After a substrate that reacts with the enzyme is added for color development, the content of the test substance in the sample could be judged by the color for qualitative or quantitative analysis.

TABLE 17

Specific lysis assay of Claudin18.2 CAR-T cells with different scFvs in vitro

| Specific lysis rate (E:T = 1:1) | T | CN01 | CN02 | CN03 | CN04 |
|---|---|---|---|---|---|
| 293T | 1.60% | 5.90% | 7.25% | 9.18% | 3.96% |
| 293T-hClaudin18.1 | 2.42% | 17.60% | 5.75% | 34.85% | 15.25% |
| 293T-hClaudin18.2 | 0.77% | 28.31% | 39.68% | 51.53% | 23.78% |

| Specific lysis rate (E:T = 3:1) | T | CN01 | CN02 | CN03 | CN04 |
|---|---|---|---|---|---|
| 293T | 1.10% | 14.91% | 19.21% | 23.08% | 8.93% |
| 293T-hClaudin18.1 | 2.72% | 30.79% | 11.98% | 44.53% | 32.91% |
| 293T-hClaudin18.2 | −0.49% | 58.02% | 55.86% | 65.62% | 49.72% |

TABLE 18

Release of IFN-gamma cytokines in supernatant of co-incubated Claudin18.2 CAR-T cells with different scFvs and different 293T cells

| IFN-gamma pg/mL (E:T = 1:1) | T | CN01 | CN02 | CN03 | CN04 |
|---|---|---|---|---|---|
| 293T | 0.00 | 0.00 | 0.00 | 578.76 | 0.00 |
| 293T-hClaudin18.1 | 0.00 | 1059.53 | 0.00 | 7229.32 | 3291.64 |
| 293T-hClaudin18.2 | 0.00 | 3818.19 | 7091.96 | 11235.69 | 7961.92 |

| IFN-gamma pg/mL (E:T = 3:1) | T | CN01 | CN02 | CN03 | CN04 |
|---|---|---|---|---|---|
| 293T | 0.00 | 17.87 | 0.00 | 899.27 | 0.00 |
| 293T-hClaudin18.1 | 0.00 | 1952.37 | 0.00 | 10411.52 | 4619.46 |
| 293T-hClaudin18.2 | 0.00 | 4791.17 | 10171.14 | 14188.95 | 8889.10 |

15 6.7.2 Target Toxicity Assay

In the example, an in vitro pharmacodynamic test was established by simulating the mechanism of action (MOA) of the product. The inventor constructed a plasmid overexpressing Claudin18.2 protein with a plvx vector, and prepared a lentivirus. Gastric cancer cells NUGC4 and AGS were infected with the lentivirus, and NUGC4 cells and AGS cells with high expression of Claudin18.2 protein were obtained through subsequent screening of positive cells as target cells for functional verification of CAR-T cells. Claudin18.2 CAR-T cells with different scFvs prepared above were used as effector cells. A co-incubation system of CAR-T cells and target tumor cells was established in different E:T (effector cells:target cells) ratios. The biological efficacy of the CAR-T cells was evaluated by measuring the lysis rate of tumor cells, with a co-incubation system of non-transduced T cells and tumor cells being the control.

Figure 16:
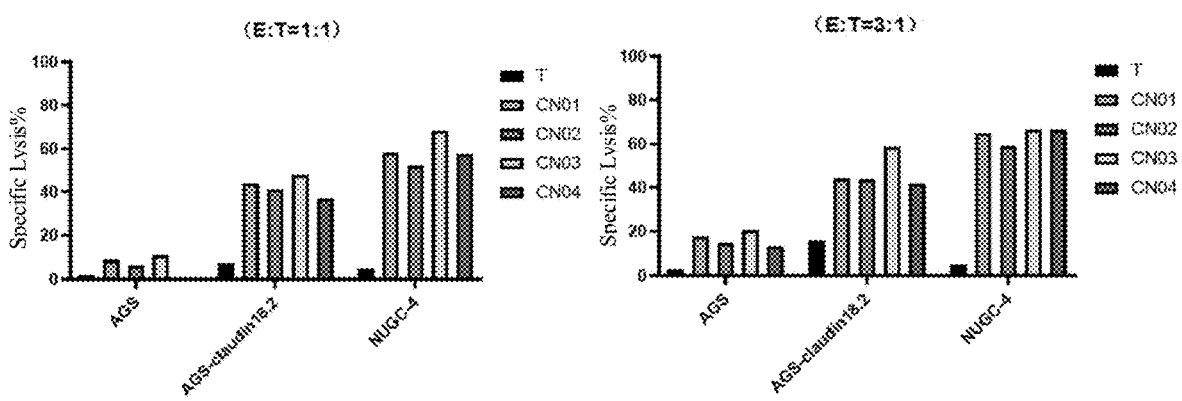
FIG. 16 shows the specific lysis assay of Claudin18.2 CAR-T cells with different scFvs against Claudin18.2-positive tumor cells.
Figure 17:
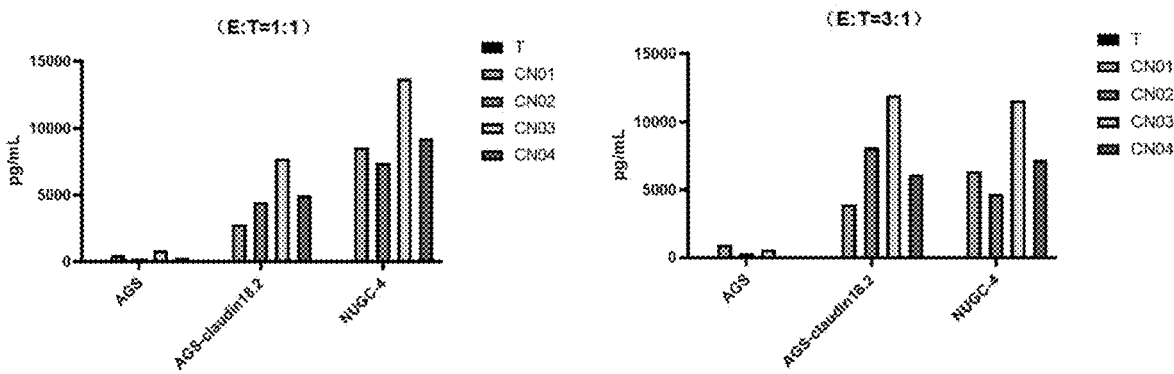
FIG. 17 shows the release of IFN-gamma cytokines in supernatant of co-incubated Claudin18.2 CAR-T cells with different scFvs and Claudin18.2-positive tumor cells.

The results of in vitro assay (FIG. 16 and Table 19) demonstrated that the efficiency of killing tumor cells was excellent at 24 h when CAR-T cells were co-incubated with Claudin18.2-positive tumor cells (AGS-claudin18.2 and NUGC-4), which was significantly higher than that of T cells, while the killing effect on the Claudin 18.2-negative cell line AGS was mild. Also, the biological efficacy of CAR-T cells was evaluated by measuring the content of cytokines (INF-gamma) secreted into the culture supernatant. After Claudin18.2 CAR-T cells were co-incubated with Claudin18.2-positive tumor cells (AGS-claudin18.2 and NUGC-4), the expression of the IFN-gamma cytokines was significantly higher than that of the T cell group (FIG. 17, Table 20).

TABLE 19

Specific lysis assay of Claudin18.2 CAR-T cells with different scFvs against Claudin18.2-positive tumor cells

| Specific lysis rate (E:T = 1:1) | T | CN01 | CN02 | CN03 | CN04 |
|---|---|---|---|---|---|
| AGS | 2.01% | 8.83% | 6.32% | 10.89% | −1.12% |
| AGS-claudin18.2 | 7.61% | 43.94% | 41.18% | 47.84% | 37.02% |
| NUGC-4 | 5.05% | 58.25% | 52.22% | 68.23% | 57.64% |

| Specific lysis rate (E:T = 3:1) | T | CN01 | CN02 | CN03 | CN04 |
|---|---|---|---|---|---|
| AGS | 3.11% | 17.53% | 14.67% | 20.50% | 13.18% |
| AGS-claudin18.2 | 15.92% | 44.20% | 43.86% | 58.56% | 41.87% |
| NUGC-4 | 5.17% | 64.78% | 59.11% | 66.50% | 66.38% |

TABLE 20

Release of IFN-gamma cytokines in supernatant of co-incubated Claudin18.2 CAR-T cells with different scFvs and Claudin18.2-positive tumor cells

| IFN-gamma pg/mL (E:T = 1:1) | T | CN01 | CN02 | CN03 | CN04 |
|---|---|---|---|---|---|
| AGS | 6.42 | 475.74 | 235.36 | 842.04 | 304.04 |
| AGS-claudin18.2 | 0.00 | 2787.98 | 4470.66 | 7732.98 | 4962.87 |
| NUGC-4 | 0.00 | 8580.04 | 7401.03 | 13731.08 | 9266.85 |

| IFN-gamma pg/mL (E:T = 3:1) | T | CN01 | CN02 | CN03 | CN04 |
|---|---|---|---|---|---|
| AGS | 63.66 | 979.40 | 349.83 | 613.10 | 0.00 |
| AGS-claudin18.2 | 0.00 | 3955.55 | 8145.06 | 11968.28 | 6130.44 |
| NUGC-4 | 0.00 | 6382.26 | 4745.38 | 11624.88 | 7206.43 |

The in vitro cytotoxicity assay shows that all the T lymphocytes expressing different chimeric antigen receptors have good killing ability on Claudin18.2-positive tumor cells, which provides a basis for pharmacodynamic studies in animals.

6.8 Studies in Animals

Figure 18:
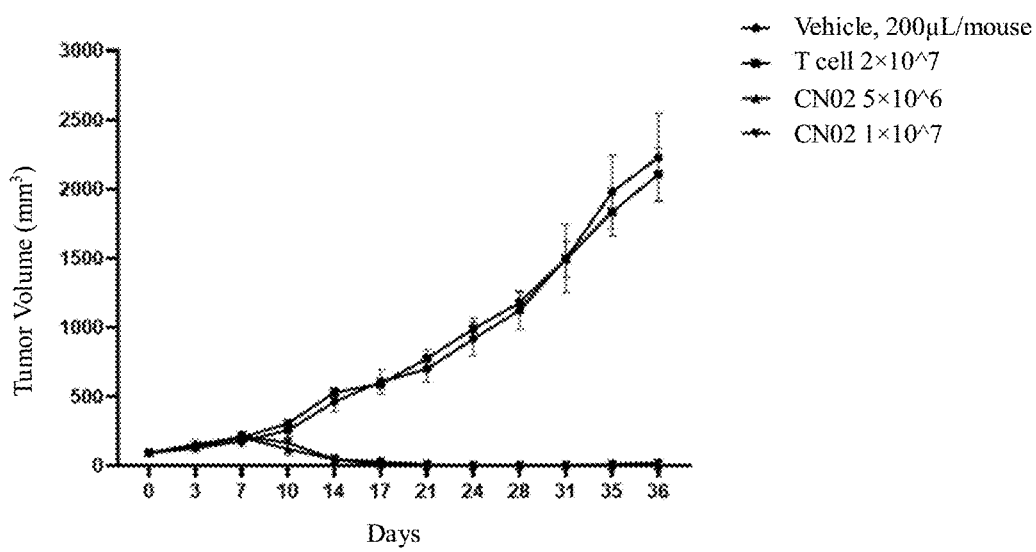
FIG. 18 shows the tumor volumes in female NOG mice bearing NUGC4-Claudin18.2 tumor cells after receiving Claudin18.2 CAR-T cells.

In the example, a pharmacodynamic model of immunodeficient mouse bearing gastric cancer tumor was established. Based on in vitro studies, each of the female NOG mice (purchased from Charles River) was grafted with $1 \times 10^7$ NUGC4-Claudin18.2 cells on the back. The mice were administered on Day 11 after grafting (the tumor volume was about 80-100 mm$^3$). The vehicle control group was administered with 0.9% normal saline, the Mock-T (T cells not transfected with plasmid) group was administered with $1 \times 10^7$ cells, and CN02 low-dose and high-dose groups (positive cells) were administered with $5.00 \times 10^6$ and $1.00 \times 10^7$ cells respectively. The dose volume was 100 μL. 6 animals were allocated in each group. Tumors were measured twice a week after administration. The tumor growth curve was plotted, TGI and T/C were calculated, and all tumors were photographed at the end of the study. Blood was sampled before CAR-T administration (Day-2), on Days 2, 9 and 28 after administration, and the vector copy number (VCN) of CAR in peripheral blood of mice was measured by qPCR, so as to confirm the expansion of CART cells. The results showed that within 36 days after CAR-T administration, the efficacy of both treatment group was significant. In the 6 mice in the Claudin18.2 CAR-T (CN02) low-dose group, the tumor regressed completely (6/6), and in 5 mice in the high-dose group, the tumor regressed completely (5/6) (FIG. 18).

Figure 19:
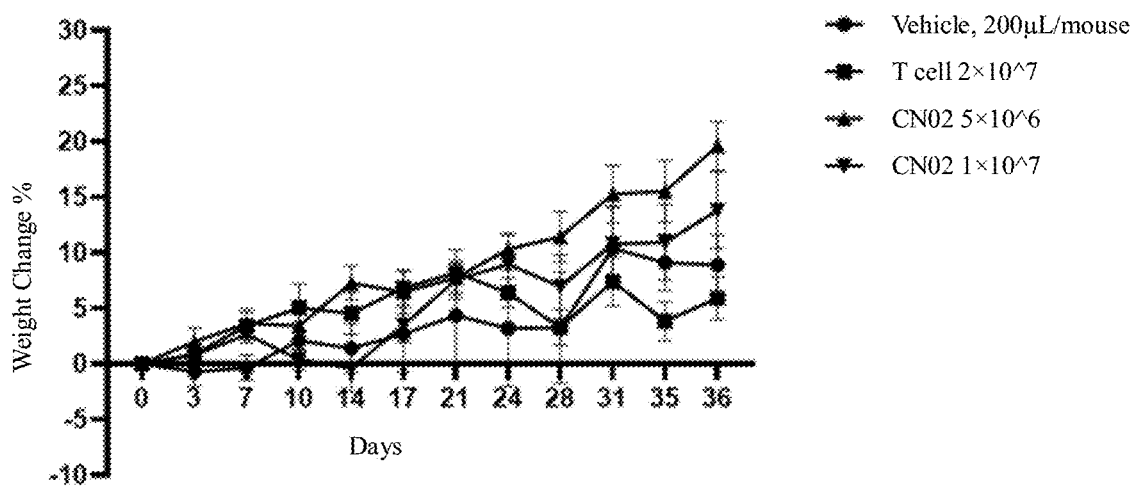
FIG. 19 shows the body weight of female NOG mice bearing NUGC4-Claudin18.2 tumor cells after receiving Claudin18.2 CAR-T cells.

(1) Body weight: compared with the vehicle control and Mock groups, the Claudin18.2 CAR-T (CN02) low-dose and high-dose groups had no significant difference in body weight (FIG. 19).

Figure 20:
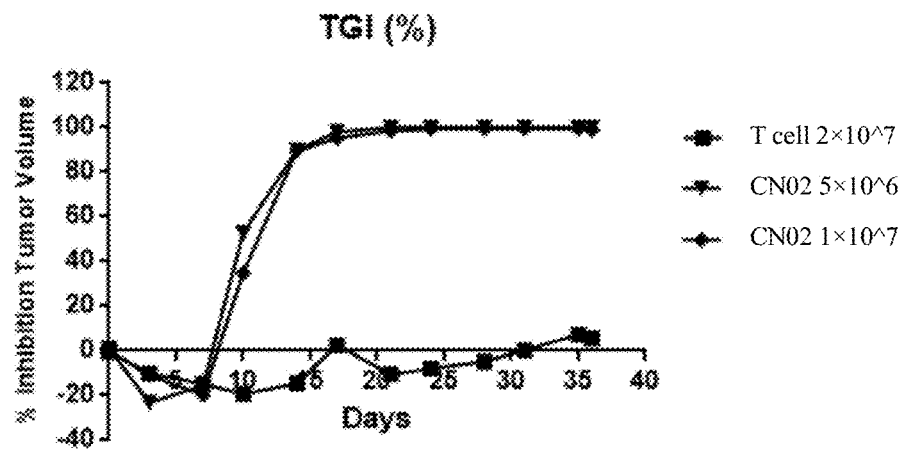
FIG. 20 shows the tumor growth inhibition (TGI) in female NOG mice bearing NUGC4-Claudin18.2 tumor cells after receiving Claudin18.2 CAR-T cells.

(2) Tumor growth inhibition (TGI): 14 days after administration, the TGI of the Claudin18.2 CAR-T (CN02) low-dose and high-dose groups was 100% and 88.33% respectively (FIG. 20).

Figure 21:
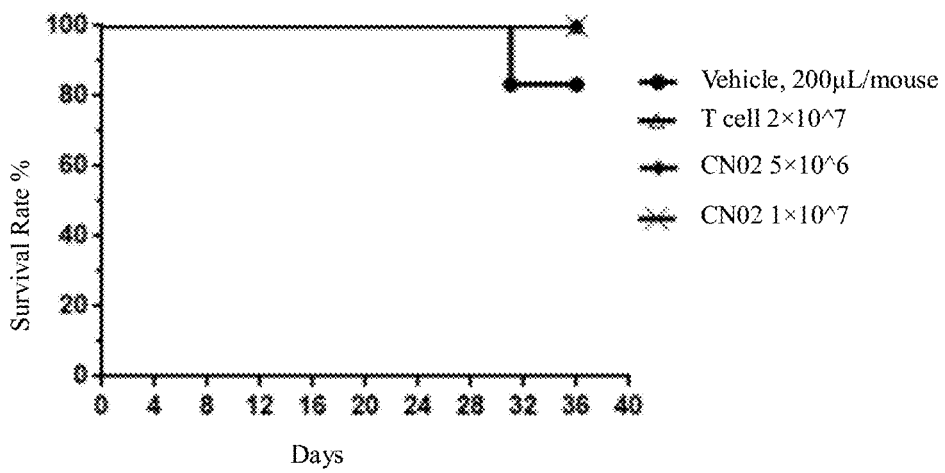
FIG. 21 shows the survival rate of female NOG mice bearing NUGC4-Claudin18.2 tumor cells after receiving Claudin18.2 CAR-T cells.

(3) Death rate: by 31 days after administration, one animal was found dead in the vehicle control group, and no death was observed in the Claudin18.2 CAR-T (CN02) low-dose and high-dose groups (FIG. 21).

Figure 24:
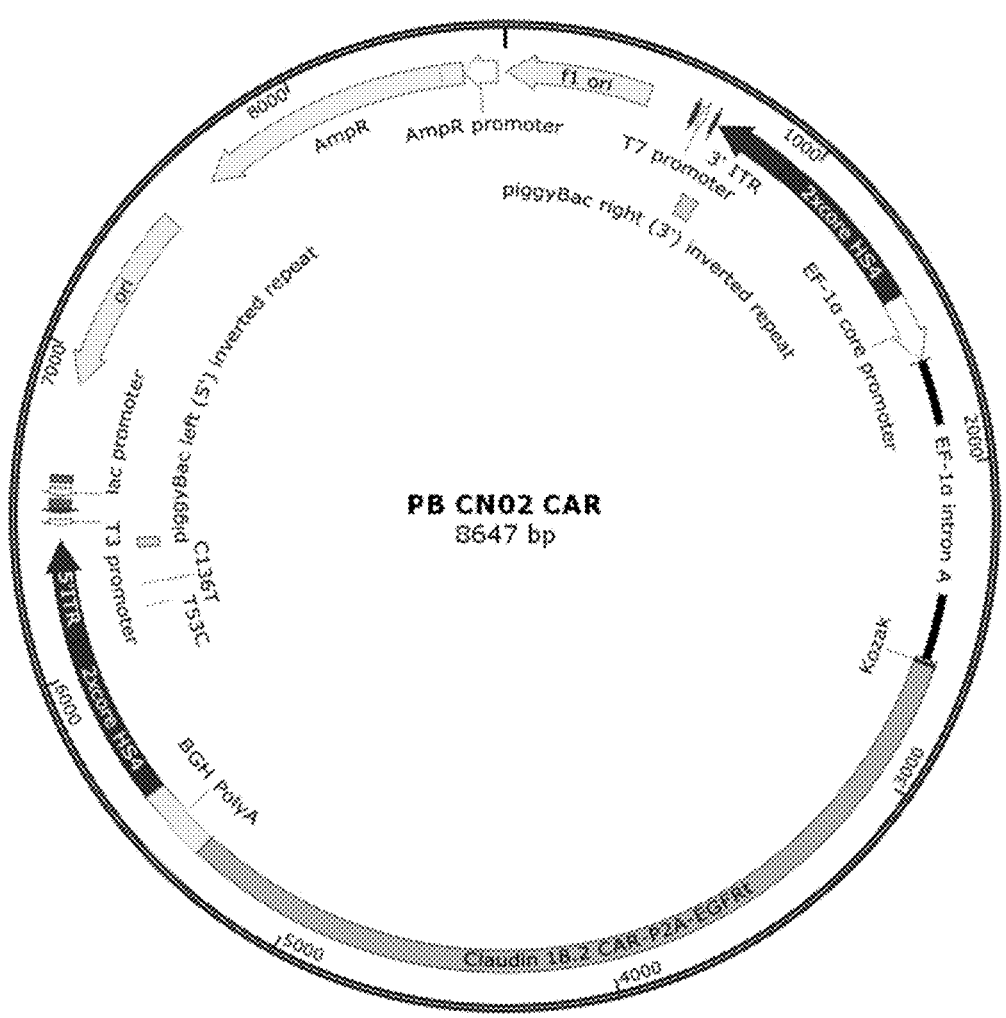
FIG. 24 shows the structural schematic of plasmid PB CN02 CAR.

16 Example 7. Preparation of CAR-T Cells by Non-Viral Method 7.1 Construction of Non-Viral PiggyBac (PB) Transposon Vector In the example, with a pBluescirpt vector (synthesized by General BIOL) as the backbone, a gene insulator sequence cHS4 was found and placed at both termini of a polyclonal site, 5'ITR and 3'ITR sequences of PB transposon were found and constructed inside the cHS4 sequence of the vector, an EF1a promoter was inserted at the 5' terminus inside the ITR, and a poly A signal was inserted at the 3' terminus. A polyclonal sequence was retained in the middle, into which a CAR-P2A-EGFRt sequence was inserted to form a PB CN02 CAR plasmid structure, as shown in FIG. 24.

7.2 Preparation of CAR-T Cells by Non-Viral PB Transposon Vector 7.2.1 Peripheral blood mononuclear cells (PBMCs) purchased from AllCells were marked with microbeads through a CD3 MicroBeads human-lyophilized Kit (purchased from Miltenyi Biotech). CD3+T lymphocytes with high purity were selected, with a proportion of CD3 positive T cells over 95%. The purified T cells were activated and proliferated using a human CD3CD28 T cell activator (Dynabeads Human T-Activator CD3/CD28, Thermo Fisher, 11132D).

7.2.2 Electroporation was performed on Day 3 after stimulation. The cells for electroporation were resuspended using a pipette and counted. $5 \times 10^6$ cells were used for each electroporation. The $5 \times 10^6$ cells were diluted with DPBS (GIBCO, 14190-144) to 4 mL, and centrifuged at 300 g at room temperature for 10 min. The supernatant was discarded, and the cells were resuspended and washed with 5 mL of DPBS, and centrifuged at 300 g at room temperature for 10 min and then the supernatant was discarded. The cells were then resuspended in 100 μL of electroporation buffer Entranster-E (Engreen, 98668-20), and the cell suspension was transferred to a 1.5-mL centrifuge tube.

The components in Table 21 were added to the centrifuge tube and mixed well.

TABLE 21

Electroporation system

| Component | Volume (μL) |
|---|---|
| PB CN02 CAR plasmid (1 μg/μL) | 5 |
| PB transposase plasmid (1 μg/μL) | 5 |
| Cell suspension | 100 |
| Total | 110 |

Electroporation was performed using an electroporation instrument manufactured by Lonza. The cell/plasmid suspension was quickly transferred to the cuvette, and the cuvette was tapped to allow the cell suspension to fully form a balanced liquid level in the cuvette. The program EO115 was used for electroporation. The cuvette was taken out carefully after electroporation. Then 500 μL of preheated T cell medium X-VIVO 15 (Lonza, 04-418Q) was added and equilibrated in an incubator at 37° C. for 5 min, and the cells were resuspended using a microporous loading tip by blowing 2-3 times. The cells were transferred to a 12-well plate containing 2 mL of preheated medium and incubated at 37° C. The medium was refreshed 4-6 h after electroporation to improve the viability. The supernatant was discarded, and preheated fresh medium was added. The cells were incubated in an incubator at 37° C./5% $CO_2$ for 48 h before the test.

Meanwhile, a CAR-T control group using lentiviruses was set. The preparation method can be seen in Section 6.6.

Figure 22:
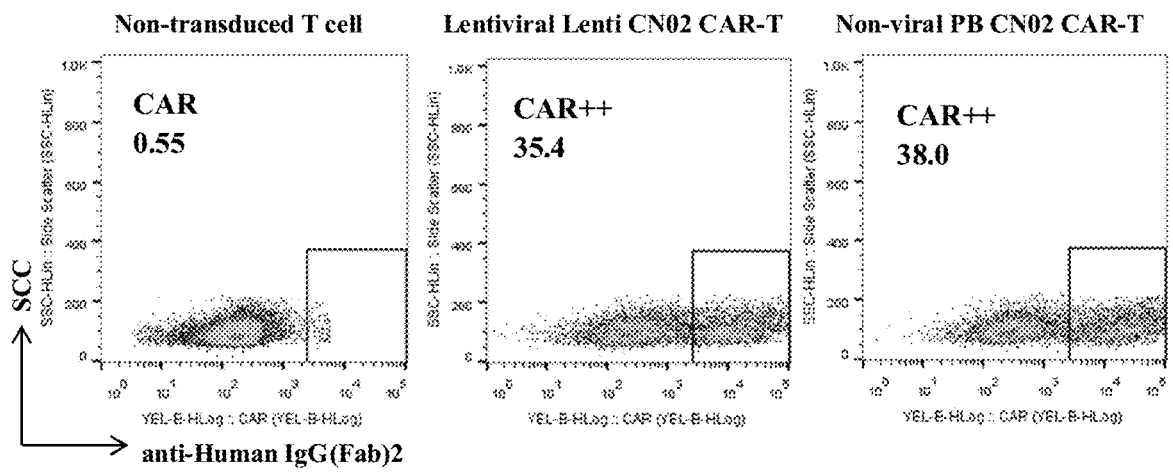
FIG. 22 shows the positive rates of T lymphocytes expressing different chimeric antigen receptors.

48-72 h after electroporation, the expression of chimeric antigen receptors was determined by flow cytometry using an anti-human IgG (Fab) 2 antibody, with non-transduced T lymphocytes as negative control. The positive rates of T lymphocytes expressing different chimeric antigen receptors are shown in Table 22 (FIG. 22).

TABLE 22

Positive rates of T lymphocytes expressing different chimeric antigen receptors

| Cell | Positive rate of CAR, % |
| --- | --- |
| Non-transduced T cell | 0.56 |
| Non-viral PB CN02 CAR-T | 35.4 |
| Lentiviral Lenti CN02 CAR-T | 38 |

7.3 Target Toxicity Assay

In the example, an in vitro pharmacodynamic test was conducted by simulating the mechanism of action (MOA) of the product. The constructed gastric cancer cells NUGC4 and AGS with high expression of Claudin18.2 were used as target cells, and CN02 CAR-T cells prepared using the above non-viral (PB) and CN02 CAR-T cells prepared using lentiviruses (*lenti*) were used as effector cells. A co-incubation system of CAR-T cells and target tumor cells was established in different E:T (effector cells:target cells) ratios. The biological efficacy of the CAR-T cells was evaluated by measuring the lysis rate of tumor cells, with a co-incubation system of non-transduced T cells and tumor cells being the control.

Figure 23:
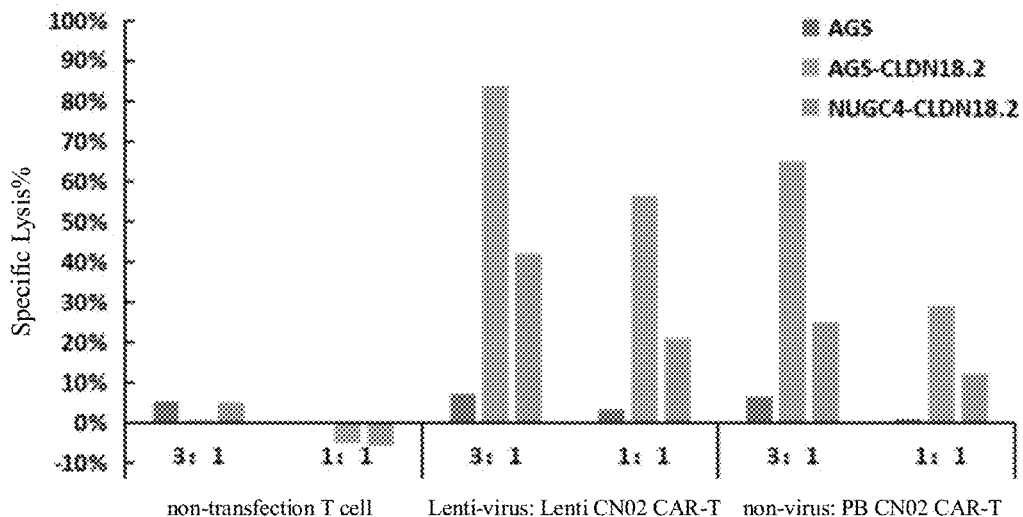
FIG. 23 shows the in vitro specific lysis assay of CN02 CAR-T cells prepared by different methods.

The results of in vitro assay (FIG. 23 and Table 23) demonstrated that the lysis rate of tumor cells was linearly correlated with the number of effector cells for a fixed number of tumor cells; and the efficiency of killing tumor cells was excellent at 24 h when CAR-T cells were co-incubated with Claudin18.2-positive tumor cells (AGS-claudin18.2 and NUGC-4), which was significantly higher than that of T cells, while the killing effect on the Claudin18.2-negative cell line AGS was mild.

TABLE 23

In vitro specific lysis assay of CN02 CAR-T cells prepared by different methods

| Specific lysis rate (E:T = 1:1) | Non-transduced T cell | Lentiviral Lenti CN02 CAR-T | Non-viral PB CN02 CAR-T |
| --- | --- | --- | --- |
| AGS | 0.23% | 3.30% | 1.12% |
| AGS-claudin18.2 | −4.79% | 56.49% | 29.28% |
| NUGC-4 | −5.50% | 21.00% | 12.00% |

| Specific lysis rate (E:T = 3:1) | Non-transduced T cell | Lentiviral Lenti CN02 CAR-T | Non-viral PB CN02 CAR-T |
| --- | --- | --- | --- |
| AGS | 5.40% | 7.20% | 6.43% |
| AGS-claudin18.2 | 0.59% | 83.83% | 64.83% |
| NUGC-4 | 5.00% | 42.00% | 25.00% |

The invention claimed is:

1. An antibody or an antigen-binding fragment thereof which binds to Claudin18.2, comprising three light chain complementarity determining regions and three heavy chain complementarity determining regions, wherein
    (1) the three light chain complementarity determining regions of the antibody or the antigen-binding fragment thereof comprise an LCDR1 set forth in SEQ ID NO: 5, an LCDR2 set forth in SEQ ID NO: 6 and an LCDR3 set forth in SEQ ID NO: 7, and the three heavy chain complementarity determining regions of the antibody or the antigen-binding fragment thereof comprise an HCDR1 set forth in SEQ ID NO: 8, an HCDR2 set forth in SEQ ID NO: 9 and an HCDR3 set forth in SEQ ID NO: 10,
    or
    (2) the three light chain complementarity determining regions of the antibody or the antigen-binding fragment thereof comprise an LCDR1 set forth in SEQ ID NO: 11, an LCDR2 set forth in SEQ ID NO: 12 and an LCDR3 set forth in SEQ ID NO: 13, and the three heavy chain complementarity determining regions of the antibody or the antigen-binding fragment thereof comprise an HCDR1 set forth in SEQ ID NO: 14, an HCDR2 set forth in SEQ ID NO: 15 and an HCDR3 set forth in SEQ ID NO: 16.

2. The antibody or an antigen-binding fragment thereof of claim 1, wherein the antibody or the antigen-binding fragment thereof comprises a light chain variable region set forth in SEQ ID NO: 1, and a heavy chain variable region set forth in SEQ ID NO: 2.

3. The antibody or the antigen-binding fragment thereof of claim 1, further comprising a heavy chain constant region set forth in SEQ ID NO: 17.

4. A chimeric antigen receptor (CAR), comprising the antibody or the antigen-binding fragment thereof of claim 1.

5. The chimeric antigen receptor of claim 4, sequentially comprising the antigen-binding fragment, an extracellular hinge region, a transmembrane region and an intracellular signaling region.

6. The chimeric antigen receptor of claim 5, wherein the extracellular hinge region is a CD8 hinge region, the transmembrane region is a CD8 transmembrane region, and the intracellular signaling region is 4-1BB and CD3ζ.

7. An isolated cell, wherein the cell expresses the CAR of claim 4.

8. A method of treating cancer, the method comprising administering to a subject in need thereof the cell of claim 7 wherein the cell is a T cell or NK cell.

9. A nucleic acid, wherein the nucleic acid encodes the antibody or the antigen-binding fragment thereof of claim 1, or a chimeric antigen receptor comprising the antigen-binding fragment.

10. An isolated cell, wherein the cell comprises the nucleic acid of claim 9.

11. A pharmaceutical composition, comprising the antibody or the antigen-binding fragment thereof of claim 1.

12. A method of treating cancer, the method comprising administering to a subject in need thereof the antibody or antigen-binding fragment thereof of claim 1.

13. The method of claim 12, wherein the cancer is a Claudin18.2-positive cancer.

14. The method of claim 12, wherein the cancer is selected from the group consisting of gastric cancer, pancreatic cancer, esophageal cancer, lung cancer, ovarian cancer, head and neck cancer, bladder cancer, cervical cancer, sarcoma, cytoma, colon cancer, kidney cancer, colorectal cancer, liver cancer, melanoma, breast cancer, myeloma, neuroglioma, leukemia and lymphoma.

15. The antibody or antigen-binding fragment thereof of claim 1, wherein the three light chain complementarity determining regions of the antibody or the antigen-binding fragment thereof comprise an LCDR1 set forth in SEQ ID NO: 5, an LCDR2 set forth in SEQ ID NO: 6 and an LCDR3 set forth in SEQ ID NO: 7, and the three heavy chain complementarity determining regions of the antibody or the antigen-binding fragment thereof comprise an HCDR1 set forth in SEQ ID NO: 8, an HCDR2 set forth in SEQ ID NO: 9 and an HCDR3 set forth in SEQ ID NO: 10.

16. The antibody or antigen-binding fragment thereof of claim 1, wherein the three light chain complementarity determining regions of the antibody or the antigen-binding fragment thereof comprise an LCDR1 set forth in SEQ ID NO: 11, an LCDR2 set forth in SEQ ID NO: 12 and an LCDR3 set forth in SEQ ID NO: 13, and the three heavy chain complementarity determining regions of the antibody or the antigen-binding fragment thereof comprise an HCDR1 set forth in SEQ ID NO: 14, an HCDR2 set forth in SEQ ID NO: 15 and an HCDR3 set forth in SEQ ID NO: 16.

17. The antibody or antigen-binding fragment thereof of claim 1, wherein the antibody or the antigen-binding fragment thereof comprises a light chain variable region set forth in SEQ ID NO: 3, and a heavy chain variable region set forth in SEQ ID NO: 4.

18. The antibody or antigen-binding fragment thereof of claim 1, further comprising a heavy chain constant region set forth in SEQ ID NO: 18.

19. An isolated cell, wherein the cell expresses the antibody or antigen-binding fragment thereof of claim 1.

20. A method of detecting Claudin18.2, the method comprising contacting a sample with the antibody or antigen-binding fragment thereof of claim 1.

* * * * *